US009515268B2

(12) United States Patent
Liu et al.

(10) Patent No.: US 9,515,268 B2
(45) Date of Patent: Dec. 6, 2016

(54) AROMATIC AMINE DERIVATIVES AND PREPARATION METHOD, USES AND ORGANIC ELECTROLUMINESCENT DEVICES THEREOF

(71) Applicant: BOE TECHNOLOGY GROUP CO., LTD., Beijing (CN)

(72) Inventors: Fei Liu, Beijing (CN); Xiaoguang Xu, Beijing (CN); Xue Gao, Beijing (CN)

(73) Assignee: BOE Technology Group Co., Ltd., Beijing (CN)

( * ) Notice: Subject to any disclaimer, the term of this patent is extended or adjusted under 35 U.S.C. 154(b) by 0 days.

(21) Appl. No.: 14/436,960

(22) PCT Filed: Sep. 3, 2014

(86) PCT No.: PCT/CN2014/085878
§ 371 (c)(1),
(2) Date: Apr. 20, 2015

(87) PCT Pub. No.: WO2015/161608
PCT Pub. Date: Oct. 29, 2015

(65) Prior Publication Data
US 2016/0087221 A1 Mar. 24, 2016

(30) Foreign Application Priority Data

Apr. 24, 2014 (CN) .............................. 201410169185

(51) Int. Cl.
*H01L 51/54* (2006.01)
*C09K 11/06* (2006.01)
(Continued)

(52) U.S. Cl.
CPC ......... *H01L 51/0061* (2013.01); *C07D 495/22* (2013.01); *C07D 519/00* (2013.01);
(Continued)

(58) Field of Classification Search
CPC ..... H05B 33/14; C09K 11/06; C09K 2211/00; C09K 2211/10; C09K 2211/1018; C09K 2211/1022; C09K 2211/1025; C09K 2211/1051; C07D 495/00; C07D 495/22; C07D 513/00; C07D 513/22; C07D 519/00; H01L 51/0032; H01L 51/005; H01L 51/0058; H01L 51/0059; H01L 51/0061; H01L 51/0062; H01L 51/0067; H01L 51/0068; H01L 51/0071; H01L 51/0072; H01L 51/0074; H01L 51/0054; H01L 51/50; H01L 51/5056
(Continued)

(56) References Cited

U.S. PATENT DOCUMENTS 7,651,746 B2     1/2010   Hudack et al.

FOREIGN PATENT DOCUMENTS

CN        1894199 A     1/2007
CN     101161765 A     4/2008
(Continued)

OTHER PUBLICATIONS

International Search Report of the International Searching Authority for PCT/CN2014/085878 with Notice of Transmittal of the International Search Report in Chinese, mailed Jan. 21, 2015.
(Continued)

*Primary Examiner* — Andrew K Bohaty
(74) *Attorney, Agent, or Firm* — Collard & Roe, P.C.

(57) ABSTRACT

The present invention relates to the field of organic electroluminescent technology, particularly relates to an aromatic amine derivative, its preparation method, uses and organic electroluminescent devices. The technical aim of the present invention is to improve the film forming ability and the redox repeatability. The aromatic amine derivative has the structure of formula I, wherein, $R_1$, $R_2$, $R_3$ and $R_4$ each independently represent a hydrogen, a substituted or unsubstituted $C_1$-$C_{40}$ alkyl, a substituted or unsubstituted $C_1$-$C_{40}$ alkoxy, a substituted or unsubstituted $C_3$-$C_{40}$ cycloalkyl, a substituted or unsubstituted $C_6$-$C_{50}$ aryl group, a substituted or unsubstituted $C_3$-$C_{50}$ heteroaryl containing one or two heteroatoms selected from N, O and S, or a substituted or unsubstituted $C_{10}$-$C_{40}$ fused aryl group formed together with the phenyl group linked therewith; wherein, m, n, p and q each independently represent 0, 1, 2, 3, 4 or 5; the substituents are one or more groups selected from the group consisting of a halogen, a $C_1$-$C_{10}$ alkyl, a $C_1$-$C_{10}$ alkoxy, a $C_3$-$C_{20}$ cycloalkyl, a $C_6$-$C_{20}$ aryl group or a $C_4$-$C_{20}$ heteroaryl group. The present invention may be applied in organic electroluminescent devices.

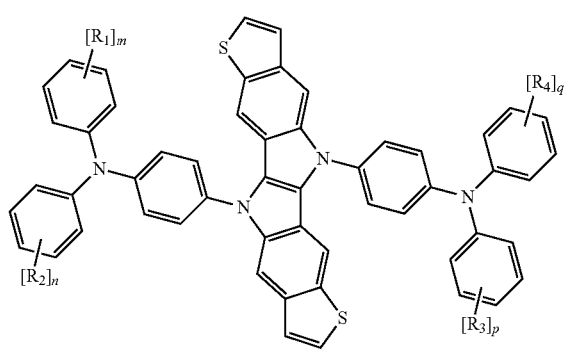

I

16 Claims, 1 Drawing Sheet

(51) Int. Cl.
  *H01L 51/00* (2006.01)
  *H05B 33/14* (2006.01)
  *C07D 495/22* (2006.01)
  *C07D 519/00* (2006.01)
  *H01L 51/50* (2006.01)

(52) U.S. Cl.
  CPC ............ C09K 11/06 (2013.01); H01L 51/006 (2013.01); H05B 33/14 (2013.01); *H01L 51/0054* (2013.01); *H01L 51/0058* (2013.01); *H01L 51/0067* (2013.01); *H01L 51/0068* (2013.01); *H01L 51/0071* (2013.01); *H01L 51/0072* (2013.01); *H01L 51/5056* (2013.01)

(58) Field of Classification Search
  USPC ....... 428/690, 691, 917, 411.4, 336; 427/58, 427/66; 313/500–512; 257/40, 88–104, 257/E51.001–E51.052; 252/301.16–301.35
  See application file for complete search history.

(56) References Cited

FOREIGN PATENT DOCUMENTS

| | | |
|---|---|---|
| CN | 103159763 A | 6/2013 |
| CN | 103214490 A | 7/2013 |
| CN | 103936653 A | 7/2014 |

OTHER PUBLICATIONS

Written Opinion of the International Searching Authority of PCT/CN2014/085878 in Chinese, mailed Jan. 21, 2015 with English translation.

AROMATIC AMINE DERIVATIVES AND PREPARATION METHOD, USES AND ORGANIC ELECTROLUMINESCENT DEVICES THEREOF

CROSS REFERENCE TO RELATED APPLICATIONS

This application is the National Stage of PCT/CN2014/085878 filed on Sep. 3, 2014, which claims priority under 35 U.S.C. §119 of Chinese Application No. 201410169185.9 filed on Apr. 24, 2014, the disclosure of which is incorporated by reference.

TECHNICAL FIELD

This application relates to the field of organic electroluminescent technology, particularly relates to an aromatic amine derivative, its preparation method, uses and organic electroluminescent devices.

BACKGROUND

Organic Light Emitting Diodes (OLED) refer to the technology of organic semiconductor material emitting light under the influence of the electric field. OLED shows promising prospects in flat panel display and lighting because of its various advantages such as self-luminescence, all solid state, low driving voltage, high efficiency, fast response, wide viewing angle, simple manufacturing process and capacity of large area and flexible display.

Generally a known OLED device structure includes a hole transporting layer, a light emitting layer, an electron transporting layer and an electron injection layer. To improve the luminous efficiency and to prolong the lifetime of the OLED device, various hole transport materials have been studied and used. For example, triarylamine, which was discovered in early age of photocopy developing technology, has high carrier mobility. However, triarylamine is not conducive to the preparation of organic electroluminescent devices for its low glass transition temperature and poor film-forming properties. Take pentacene compounds as another example, they exhibit high carrier mobility, but such substances have high HOMO level, and do not have stable redox repeatability, which results in short lifetime of the organic electroluminescent devices prepared.

SUMMARY

The main objective of the present application is to provide an aromatic amine derivative having good film forming ability and stable redox repeatability, its preparation method, uses and organic electroluminescent devices.

To achieve the above objective, the present application provides an aromatic amine derivative having the general formula I:

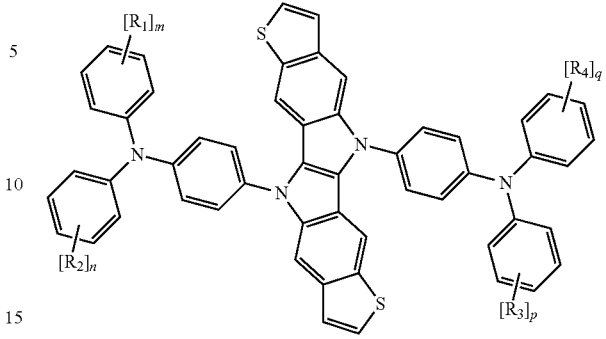

$R_1$, $R_2$, $R_3$ and $R_4$ each independently represent a hydrogen, a substituted or unsubstituted $C_1$-$C_{40}$ alkyl, a substituted or unsubstituted $C_1$-$C_{40}$ alkoxy, a substituted or unsubstituted $C_3$-$C_{40}$ cycloalkyl, a substituted or unsubstituted $C_6$-$C_{50}$ aryl group, or a substituted or unsubstituted $C_3$-$C_{50}$ heteroaryl containing one or two heteroatoms selected from N, O and S, or form a substituted or unsubstituted $C_{10}$-$C_{40}$ fused aryl group together with the phenyl group linked therewith;

wherein, m, n, p and q each independently represent 0, 1, 2, 3, 4 or 5;

the substituents are one or more groups selected from the group consisting of a halogen, a $C_1$-$C_{10}$ alkyl, a $C_1$-$C_{10}$ alkoxy, a $C_3$-$C_{20}$ cycloalkyl, a $C_6$-$C_{20}$ aryl group or a $C_4$-$C_{20}$ heteroaryl group.

Optionally, $R_1$, $R_2$, $R_3$ and $R_4$ each independently represent a hydrogen, a substituted or unsubstituted $C_1$-$C_6$ alkyl, a substituted or unsubstituted $C_1$-$C_6$ alkoxy, a substituted or unsubstituted $C_3$-$C_6$ cycloalkyl, a substituted or unsubstituted $C_6$-$C_{18}$ aryl, or a substituted or unsubstituted $C_4$-$C_{10}$ heteroaryl containing one or two heteroatoms selected from N, O and S, or form a substituted or unsubstituted $C_{10}$-$C_{18}$ fused aryl group together with the phenyl group linked therewith;

m, n, p and q each independently represent 0, 1, 2 or 3;

the substituents are one or more groups selected from the group consisting of a $C_1$-$C_6$ alkyl, a $C_1$-$C_6$ alkoxy or a $C_6$-$C_{18}$ aryl.

Optionally, $[R_1]_m$ and $[R_2]_n$ are identical to $[R_3]_p$ and $[R_4]_q$, respectively; and the substitution positions on the phenyls of $[R_1]_m$ and $[R_2]_n$ are identical to those of $[R_3]_p$ and $[R_4]_q$, respectively.

And optionally, $[R_1]_m$, $[R_2]_n$, $[R_3]_p$ and $[R_4]_q$ are the same, and the substitution positions of $[R_1]_m$, $[R_2]_n$, $[R_3]_p$ and $[R_4]_q$ on the phenyls are the same.

An embodiment of the present invention provides a method for preparing said aromatic amine derivatives, comprising:

adding 5,11-disubstituted thieno[3',2':5,6]indolo [3,2-b]thieno[3,2-f]indole (formula II), triarylamine of the formula III and/or IV, a catalyst, a base and a solvent into a reaction vessel and mixing them; wherein, X and Y independently represents a halogen;

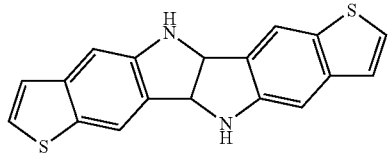

II

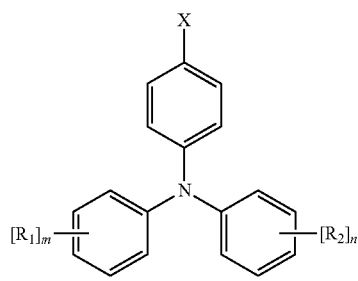

III

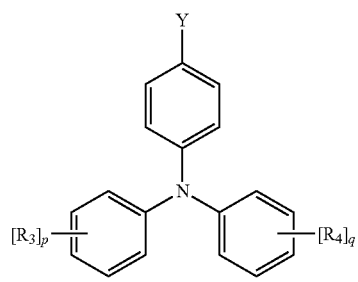

IV refluxing the obtained mixture under stirring to produce an aromatic amine derivative of the formula I, wherein $R_1$, $R_2$, $R_3$, $R_4$, m, n, p and q are as defined for formula I.

Optionally, the triarylamine of the formula III has the same structure as the triarylamine of the formula IV. In this case, adding 5,11-disubstituted thieno[3',2':5,6]indolo [3,2-b]thieno[3,2-f]indole (formula II), the triarylamine of the formulae III and IV and a solvent into the reaction vessel and mixing them; wherein, X and Y independently represents a halogen;

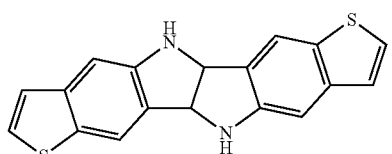

II

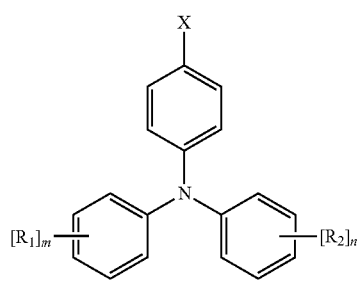

III

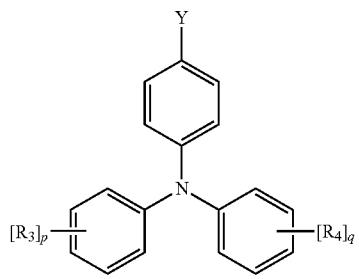

IV refluxing the obtained mixture under stirring to produce an aromatic amine derivative of the formula I.

Further optionally, the molar ratio of 5,11-disubstituted thieno[3',2':5,6]indolo [3,2-b]thieno[3,2-f]indole (formula II) to the triarylamine is from 1:2 to 1:4.

And optionally, the triarylamine of formula III is different from the triarylamine of formula IV, and the manufacturing process comprises:

adding 5,11-disubstituted thieno[3',2':5,6]indolo [3,2-b]thieno[3,2-f]indole (formula II), the triarylamine of the formula III or IV, a catalyst, a base and a solvent into a reaction vessel and mixing them;

refluxing the obtained mixture under stirring to produce a one-side substituted intermediate product substituted (formula V).

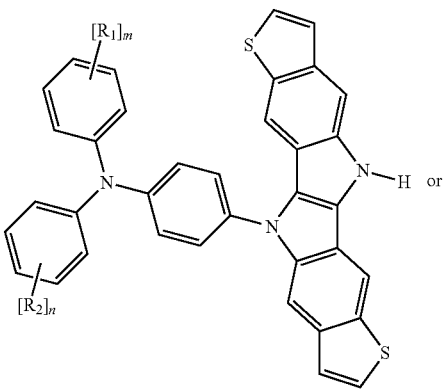

V

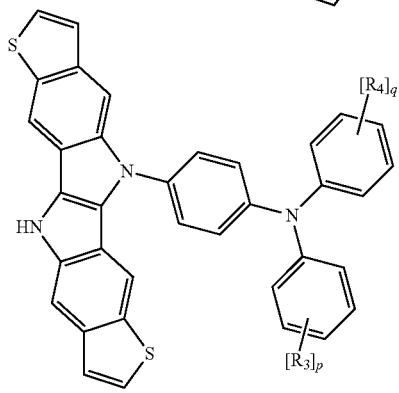

adding the one-side substituted intermediate product (formula V), the triarylamine of the formula IV or III, a catalyst, a base and a solvent into a reaction vessel and mixing them;

refluxing the obtained mixture under stirring to produce an aromatic amine derivative of the formula I.

During preparation, a catalyst is added in the reaction vessel. The catalyst further comprises a phase transfer catalyst.

Further optionally, the molar ratio of 5,11-disubstituted thieno[3',2':5,6]indolo [3,2-b]thieno[3,2-f]indole (formula II) to the triarylamine of formula III or IV is from 1:1 to 1:2;

the molar ratio of the one-side substituted intermediate product (formula V) to the triarylamine of formula IV or III is from 1:1 to 1:2.

An embodiment of the present invention provides an application of said aromatic amine derivative as hole transport materials.

An embodiment of the present invention provides an organic electroluminescent device comprising a cathode, at least one light emitting unit and an anode, wherein said light emitting unit comprises a hole transporting layer comprising said aromatic amine derivative provided by embodiments of the present invention.

Embodiments of the present invention provide an aromatic amine derivative, its preparation method, uses and organic electroluminescent devices. In the molecular structure of said aromatic amine derivative, the linearly extending π-conjugation system is connected with a non-planar, high molecular weight arylamino group, which results in large space structure, high glass transition temperature and good side film forming property of the aromatic amine derivative. Furthermore, since the molecular weight of the aromatic amine derivative is high, good thermal stability is also obtained. A heterocyclic aromatic ring with N, S, etc. has been introduced into the linearly extending π-conjugation system of the aromatic amine derivative, so that, the chemical activity of the molecule has been reduced while the carrier transporting characteristics are maintained, i.e., the oxidation and reduction repeatability has been increased, resulting in long life of the organic electroluminescent devices using the aromatic amine derivative.

BRIEF DESCRIPTION OF THE DRAWINGS

In order to more clearly explain the technical solutions of the embodiments of the present invention or the technical solutions from the prior art, some drawings related to the embodiments of the invention or the prior art will be briefly described below. Apparently, the drawings described below merely involve some embodiments of the present invention. A person of ordinary skill may obtain other drawings on the basis of these drawings without creative efforts.

DETAILED DESCRIPTION

Figure 1:
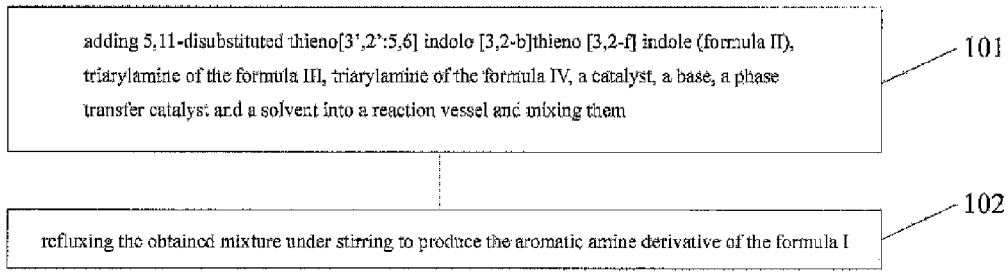
FIG. 1 is a flowchart showing a manufacture process of an aromatic amine derivative provided by an embodiment of the present invention.

The technical solutions of the embodiments of the present invention will be clearly and fully described below in connection with the drawings in the embodiments of the present invention. Obviously, the embodiments described are merely part of the embodiments of the present invention, but not all the embodiments. Based on the embodiments of the present invention, all the other embodiments within the protection scope of the present invention that can be obtained by a person skilled in the art without any creative efforts are protected by the present invention.

The aromatic amine derivative and its preparation method, uses and organic electroluminescent device of the embodiments of the present invention will be described below in detail in conjunction with the drawings.

This application provides an aromatic amine derivative of the formula I:

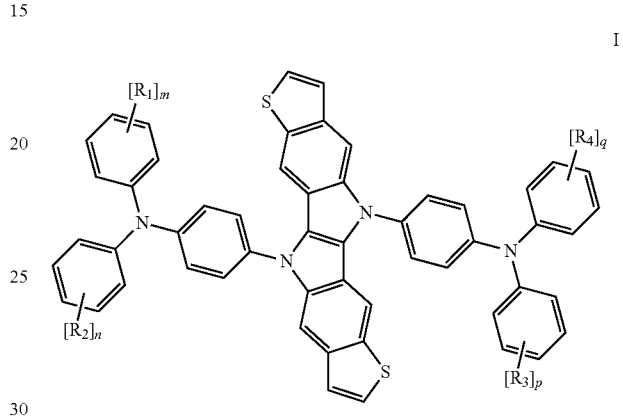

$R_1$, $R_2$, $R_3$ and $R_4$ each independently represent a hydrogen, a substituted or unsubstituted $C_1$-$C_{40}$ alkyl, a substituted or unsubstituted $C_1$-$C_{40}$ alkoxy, a substituted or unsubstituted $C_3$-$C_{40}$ cycloalkyl, a substituted or unsubstituted $C_6$-$C_{50}$ aryl group, a substituted or unsubstituted $C_3$-$C_{50}$ heteroaryl containing one or two heteroatoms selected from N, O and S, or form a substituted or unsubstituted $C_{10}$-$C_{40}$ fused aryl group together with a phenyl group linked therewith; wherein, m, n, p and q each independently represent 0, 1, 2, 3, 4 or 5; the substituents are one or more groups selected from the group consisting of a halogen, a $C_1$-$C_{10}$ alkyl, a $C_1$-$C_{10}$ alkoxy, a $C_3$-$C_{20}$ cycloalkyl, a $C_6$-$C_{20}$ aryl group or a $C_4$-$C_{20}$ heteroaryl group.

As can be seen from the formula I, the position of $R_1$ on the respective phenyl group is not constrained. For example, when $R_1$ is connected via a single bond to the phenyl, $R_1$ can be at a para-, ortho- or meta-position with respect to the N atom on the triarylamine group.

m may be 0, 1, 2, 3, 4 or 5, indicating that more than one $R_1$ may be present on the phenyl group, i.e., $R_1$ may be at mono-substituted, di-substituted, tri-substituted, tetrad-substituted or even pent-substituted position on the phenyl through connection to the phenyl via a single bond. In the case of di-substitution, tri-substitution, tetra-substitution or pent-substitution, $R_1$, including the occurrence of $R_1$ as "-idene" or "-idyne", may be connected to the phenyl group via two or three single bonds. The description above is also applicable to $R_2$, $R_3$ and $R_4$.

Besides connecting to the phenyl group via a single bond as described above, R1 may form a $C_{10}$-$C_{40}$ fused aryl group together with the phenyl. This also applies to $R_2$, $R_3$ and $R_4$.

For example, the aromatic amine derivative provided by the embodiments can be selected from those exemplified in Table 1.

TABLE 1

| | Structure |
|---|---|
| I-1 | 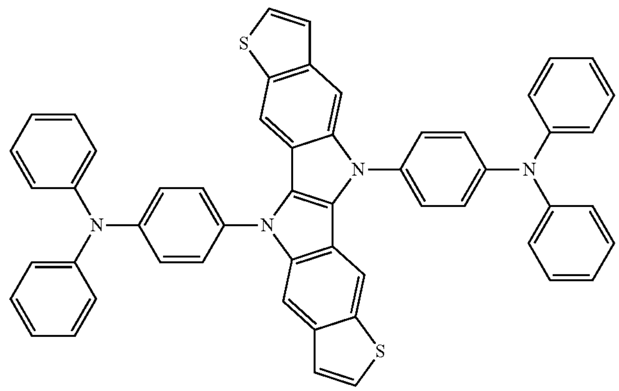 [SMILES: c1ccc(N(c2ccccc2)c2ccc(-n3c4cc5ccsc5cc4c4c3c3cc5sccc5cc3n4-c3ccc(N(c4ccccc4)c4ccccc4)cc3)cc2)cc1] |
| I-2 | 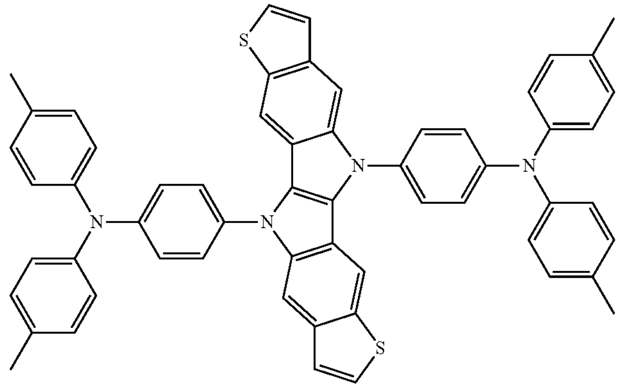 [SMILES: Cc1ccc(N(c2ccc(C)cc2)c2ccc(-n3c4cc5ccsc5cc4c4c3c3cc5sccc5cc3n4-c3ccc(N(c4ccc(C)cc4)c4ccc(C)cc4)cc3)cc2)cc1] |
| I-3 | 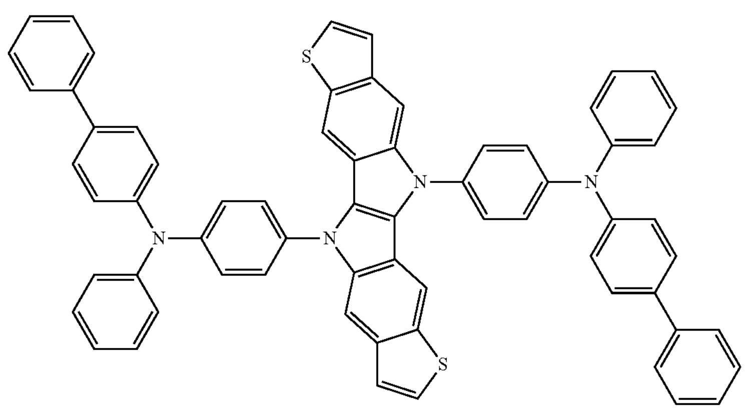 [SMILES: c1ccc(-c2ccc(N(c3ccccc3)c3ccc(-n4c5cc6ccsc6cc5c5c4c4cc6sccc6cc4n5-c4ccc(N(c5ccccc5)c5ccc(-c6ccccc6)cc5)cc4)cc3)cc2)cc1] |
| I-4 | 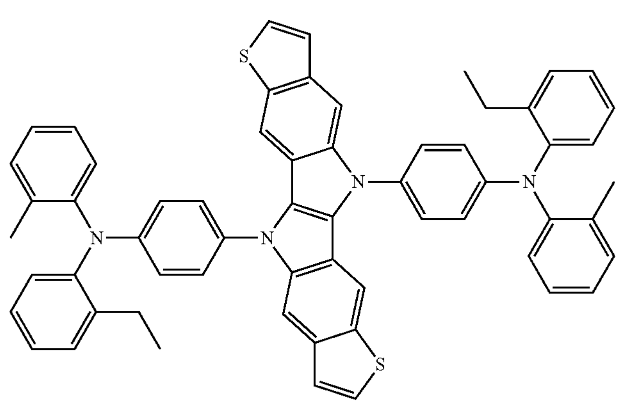 [SMILES: CCc1ccccc1N(c1ccc(-n2c3cc4ccsc4cc3c3c2c2cc4sccc4cc2n3-c2ccc(N(c3ccccc3C)c3ccccc3CC)cc2)cc1)c1ccccc1C] |

TABLE 1-continued
| Structure |
|---|
| I-5 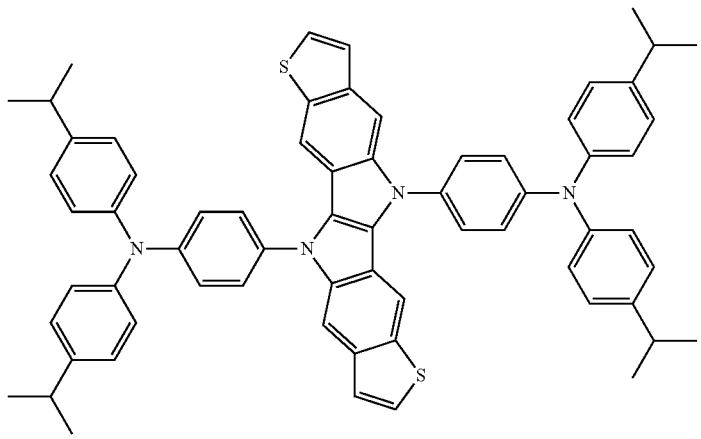 [SMILES: CC(C)c1ccc(N(c2ccc(C(C)C)cc2)c2ccc(-n3c4cc5ccsc5cc4c4c3c3cc5sccc5cc3n4-c3ccc(N(c4ccc(C(C)C)cc4)c4ccc(C(C)C)cc4)cc3)cc2)cc1] |
| I-6 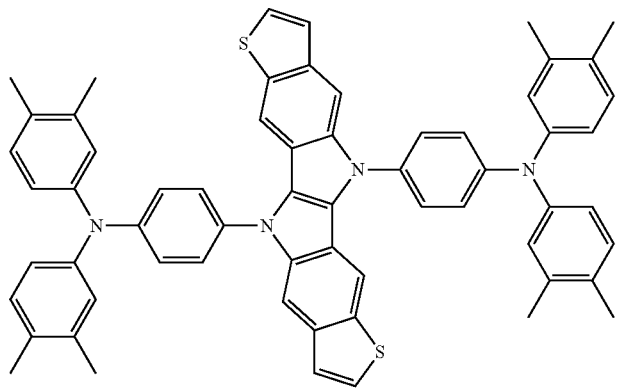 [SMILES: Cc1ccc(N(c2ccc(-n3c4cc5ccsc5cc4c4c3c3cc5sccc5cc3n4-c3ccc(N(c4ccc(C)c(C)c4)c4ccc(C)c(C)c4)cc3)cc2)c2ccc(C)c(C)c2)cc1C] |
| I-7 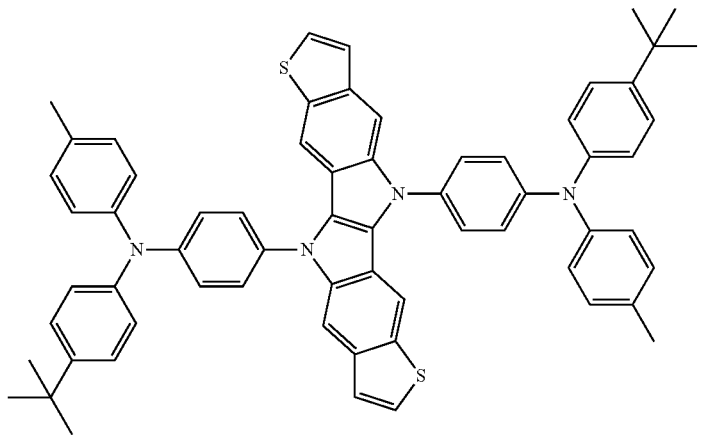 [SMILES: Cc1ccc(N(c2ccc(-n3c4cc5ccsc5cc4c4c3c3cc5sccc5cc3n4-c3ccc(N(c4ccc(C)cc4)c4ccc(C(C)(C)C)cc4)cc3)cc2)c2ccc(C(C)(C)C)cc2)cc1] |

TABLE 1-continued
Structure
I-8
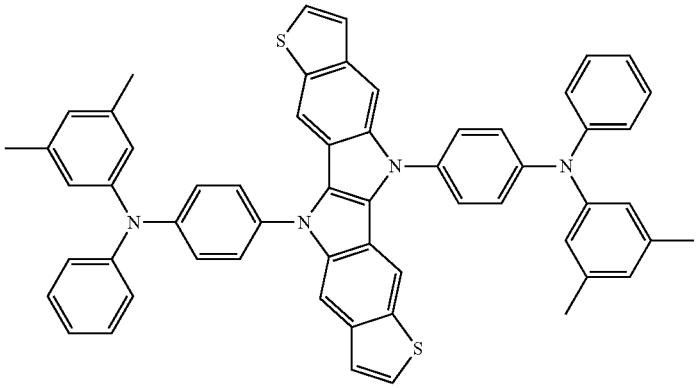
I-9
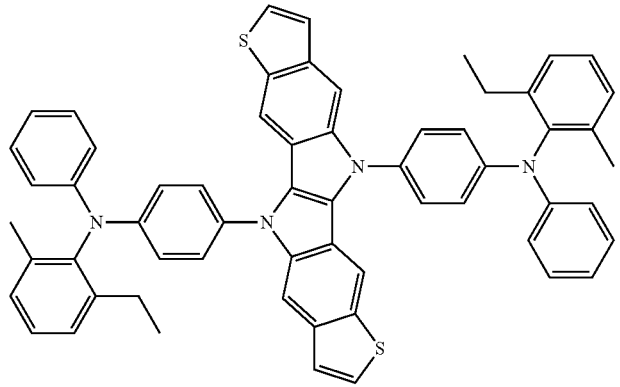 [SMILES: CCc1cccc(C)c1N(c1ccccc1)c1ccc(-n2c3cc4ccsc4cc3c3c2c2cc4sccc4cc2n3-c2ccc(N(c3ccccc3)c3c(C)cccc3CC)cc2)cc1]
I-10
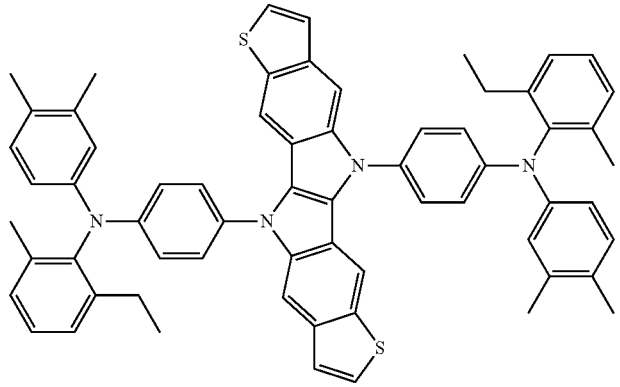 [SMILES: CCc1cccc(C)c1N(c1ccc(-n2c3cc4ccsc4cc3c3c2c2cc4sccc4cc2n3-c2ccc(N(c3ccc(C)c(C)c3)c3c(C)cccc3CC)cc2)cc1)c1ccc(C)c(C)c1]
I-11
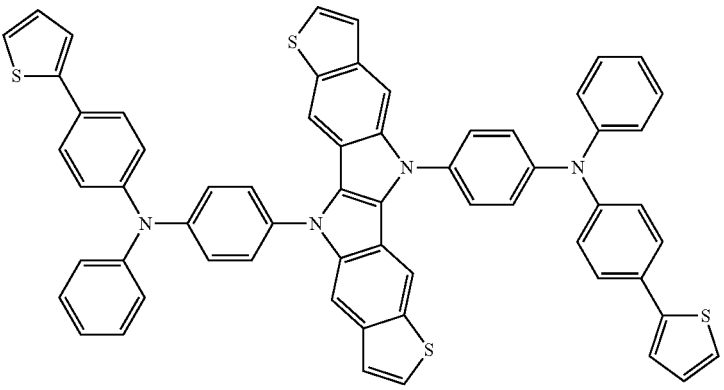 [SMILES: c1ccc(N(c2ccc(-c3cccs3)cc2)c2ccc(-n3c4cc5ccsc5cc4c4c3c3cc5sccc5cc3n4-c3ccc(N(c4ccccc4)c4ccc(-c5cccs5)cc4)cc3)cc2)cc1]

TABLE 1-continued
Structure
I-12
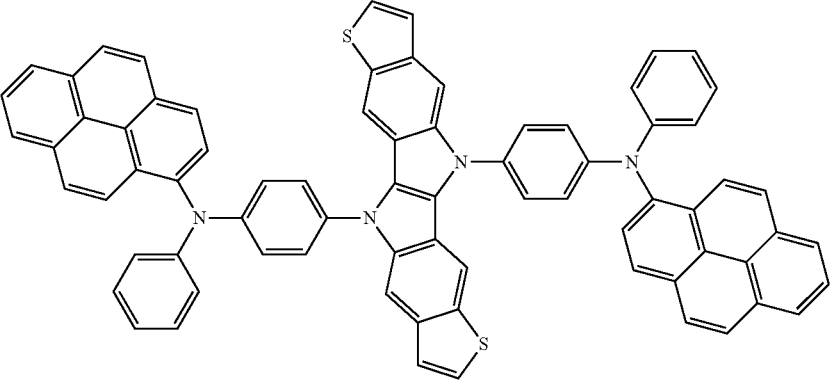 [SMILES: c1ccc(N(c2ccc(-n3c4cc5ccsc5cc4c4c3c3cc5sccc5cc3n4-c3ccc(N(c4ccccc4)c4ccc5ccc6cccc7ccc4c5c67)cc3)cc2)c2ccc3ccc4cccc5ccc2c3c45)cc1]
I-13
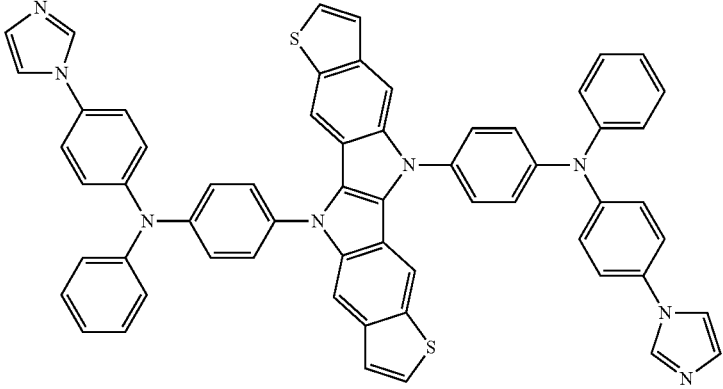 [SMILES: c1ccc(N(c2ccc(-n3ccnc3)cc2)c2ccc(-n3c4cc5ccsc5cc4c4c3c3cc5sccc5cc3n4-c3ccc(N(c4ccccc4)c4ccc(-n5ccnc5)cc4)cc3)cc2)cc1]
I-14
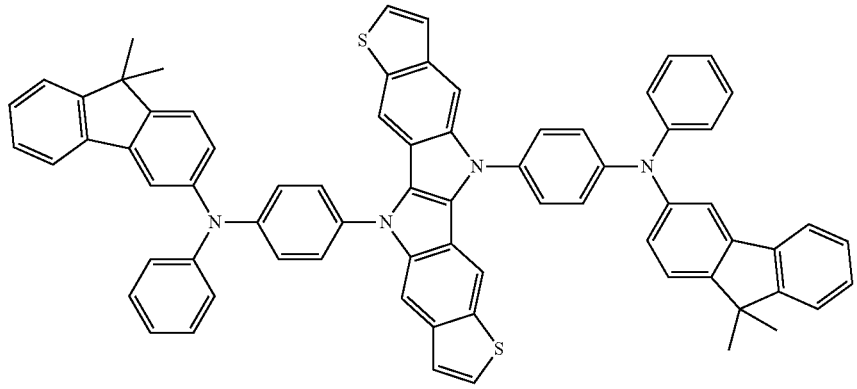 [SMILES: CC1(C)c2ccccc2-c2cc(N(c3ccccc3)c3ccc(-n4c5cc6ccsc6cc5c5c4c4cc6sccc6cc4n5-c4ccc(N(c5ccccc5)c5ccc6c(c5)-c5ccccc5C6(C)C)cc4)cc3)ccc21]
I-15
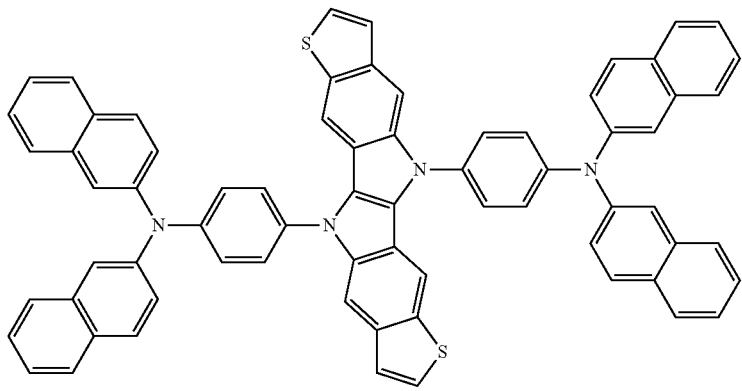 [SMILES: c1ccc2cc(N(c3ccc(-n4c5cc6ccsc6cc5c5c4c4cc6sccc6cc4n5-c4ccc(N(c5ccc6ccccc6c5)c5ccc6ccccc6c5)cc4)cc3)c3ccc4ccccc4c3)ccc2c1]

TABLE 1-continued
Structure
I-16
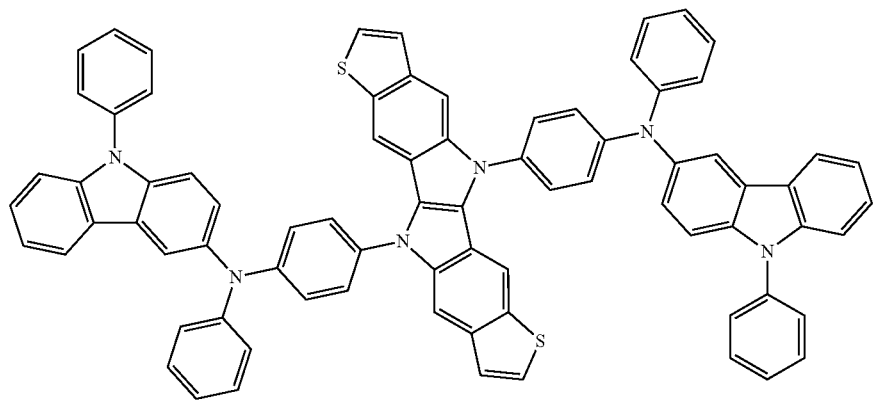 [SMILES: c1ccc(N(c2ccc(-n3c4cc5ccsc5cc4c4c3c3cc5sccc5cc3n4-c3ccc(N(c4ccccc4)c4ccc5c(c4)c4ccccc4n5-c4ccccc4)cc3)cc2)c2ccc3c(c2)c2ccccc2n3-c2ccccc2)cc1]
I-17
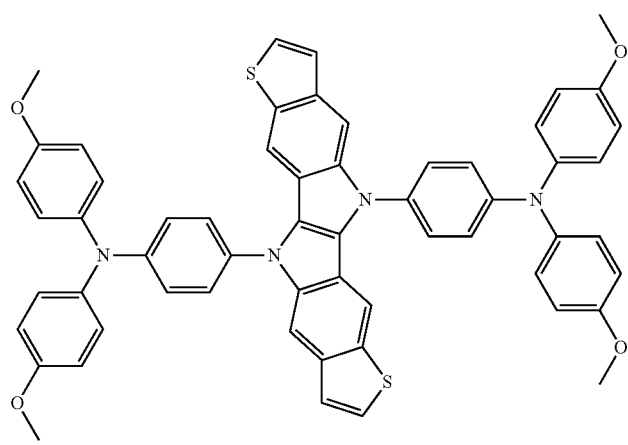 [SMILES: COc1ccc(N(c2ccc(OC)cc2)c2ccc(-n3c4cc5ccsc5cc4c4c3c3cc5sccc5cc3n4-c3ccc(N(c4ccc(OC)cc4)c4ccc(OC)cc4)cc3)cc2)cc1]
I-18
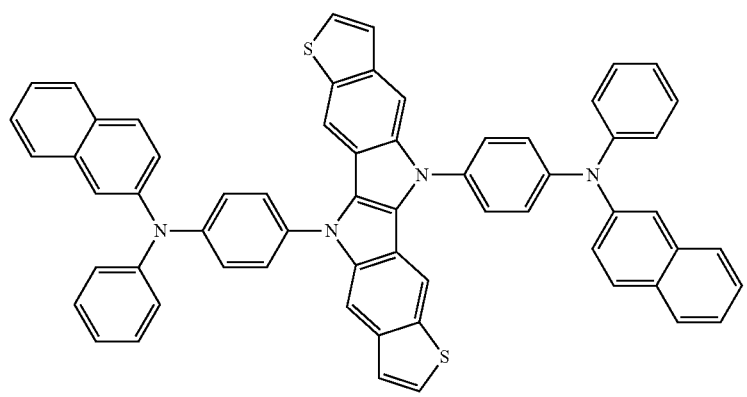 [SMILES: c1ccc(N(c2ccc(-n3c4cc5ccsc5cc4c4c3c3cc5sccc5cc3n4-c3ccc(N(c4ccccc4)c4ccc5ccccc5c4)cc3)cc2)c2ccc3ccccc3c2)cc1]

TABLE 1-continued
Structure
I-19
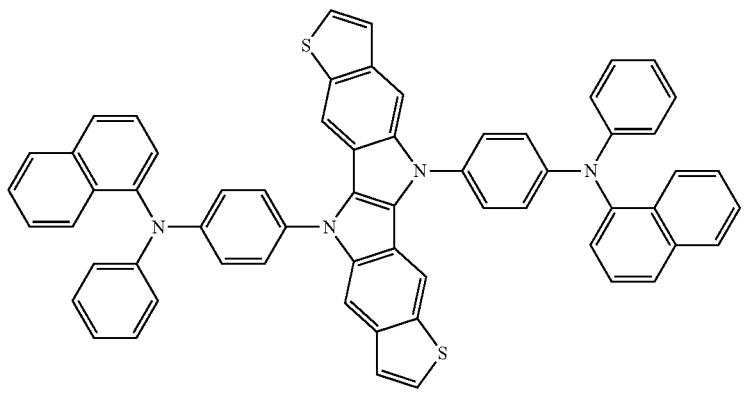 [SMILES: c1ccc(N(c2ccc(-n3c4cc5ccsc5cc4c4c3c3cc5sccc5cc3n4-c3ccc(N(c4ccccc4)c4cccc5ccccc45)cc3)cc2)c2cccc3ccccc23)cc1]
I-20
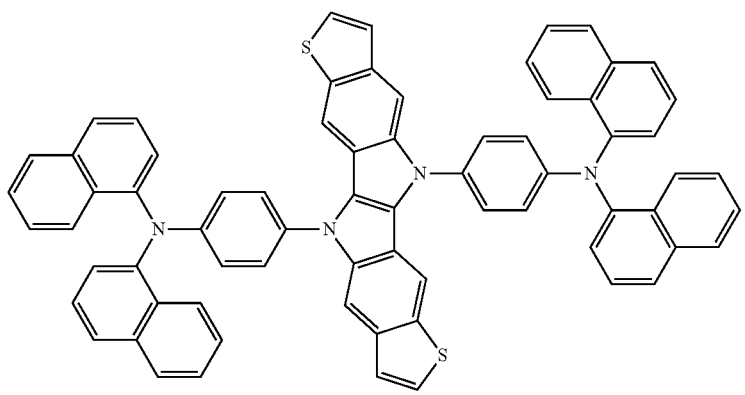 [SMILES: c1ccc2c(N(c3ccc(-n4c5cc6ccsc6cc5c5c4c4cc6sccc6cc4n5-c4ccc(N(c5cccc6ccccc56)c5cccc6ccccc56)cc4)cc3)c3cccc4ccccc34)cccc2c1]
I-21
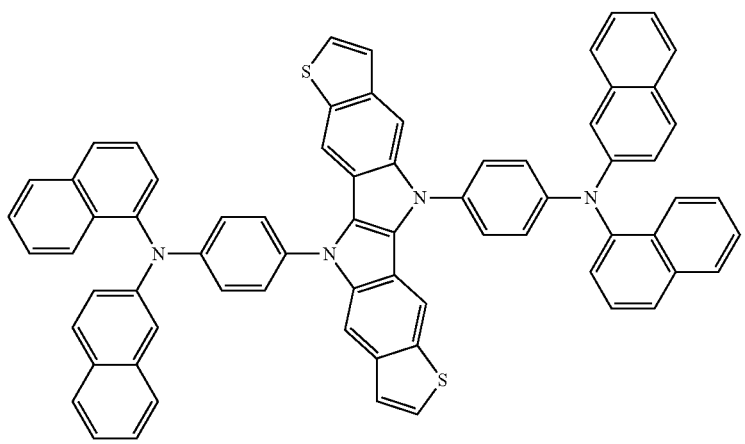 [SMILES: c1ccc2cc(N(c3ccc(-n4c5cc6ccsc6cc5c5c4c4cc6sccc6cc4n5-c4ccc(N(c5ccc6ccccc6c5)c5cccc6ccccc56)cc4)cc3)c3cccc4ccccc34)ccc2c1]

TABLE 1-continued
Structure
I-22
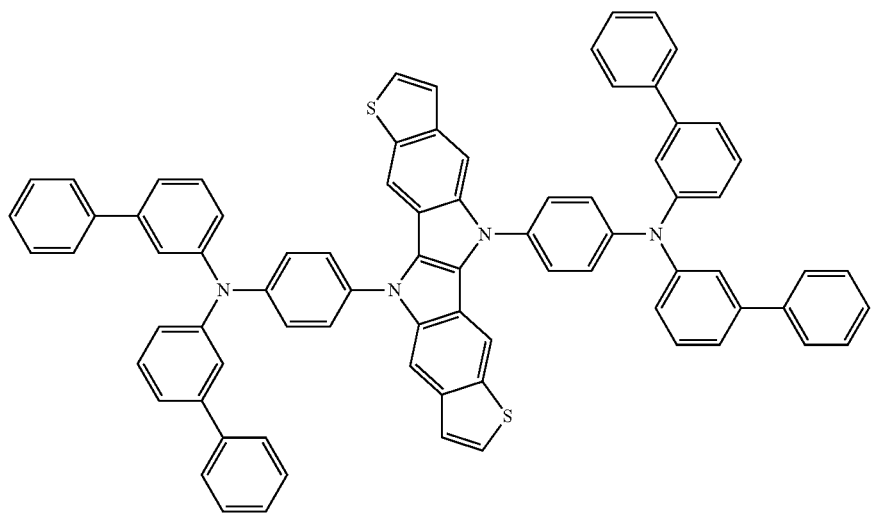 [SMILES: c1ccc(-c2cccc(N(c3ccc(-n4c5cc6ccsc6cc5c5c4c4cc6sccc6cc4n5-c4ccc(N(c5cccc(-c6ccccc6)c5)c5cccc(-c6ccccc6)c5)cc4)cc3)c3cccc(-c4ccccc4)c3)c2)cc1]
I-23
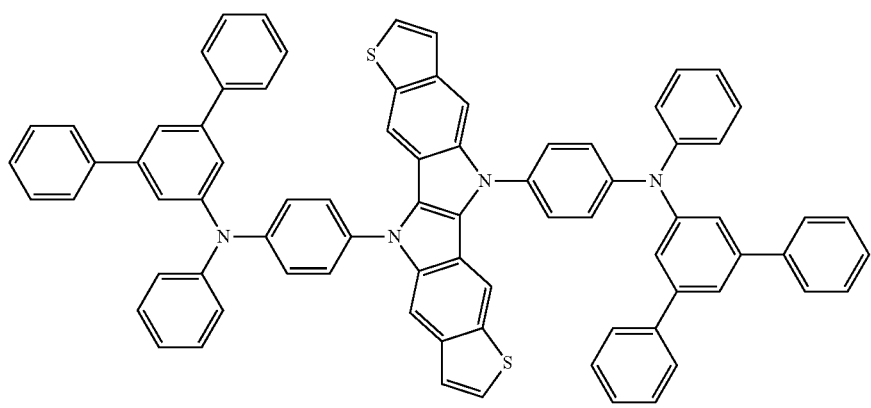 [SMILES: c1ccc(-c2cc(-c3ccccc3)cc(N(c3ccccc3)c3ccc(-n4c5cc6ccsc6cc5c5c4c4cc6sccc6cc4n5-c4ccc(N(c5ccccc5)c5cc(-c6ccccc6)cc(-c6ccccc6)c5)cc4)cc3)c2)cc1]
I-24
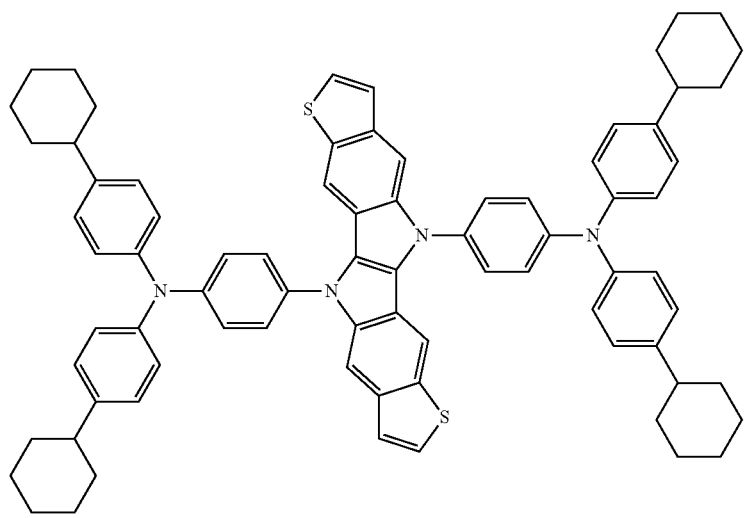 [SMILES: c1cc2cc3c(cc2s1)c1c(c2cc4sccc4cc2n1-c1ccc(N(c2ccc(C4CCCCC4)cc2)c2ccc(C4CCCCC4)cc2)cc1)n3-c1ccc(N(c2ccc(C3CCCCC3)cc2)c2ccc(C3CCCCC3)cc2)cc1]

TABLE 1-continued

Structure

I-25

I-26

I-27

TABLE 1-continued

Structure

I-28

I-29

I-30

It should be understood that aromatic amine derivatives provided above are only exemplificative and do not limit the scope of the present invention.

In the molecular structure of the aromatic amine derivatives provided by the embodiments of the present invention, the linearly extending π-conjugation system is connected with a non-planar, high molecular weight arylamino group, which results in large space structure, high glass transition temperature and good side film forming property of the aromatic amine derivatives. Furthermore, since the molecular weight of the aromatic amine derivatives is high, good thermal stability is also obtained. A heterocyclic aromatic ring with N, S, etc. has been introduced into the linearly extending π-conjugation system of the aromatic amine derivatives, so that, the chemical activity of the molecule has been reduced while the carrier transporting characteristics are maintained, i.e., the oxidation and reduction repeatability has been increased, resulting in long life of the organic electroluminescent devices using the aromatic amine derivatives.

Further optionally, in another embodiment of the present invention, the $R_1$, $R_2$, $R_3$ and $R_4$ each independently represent a hydrogen, a substituted or unsubstituted $C_1$-$C_6$ alkyl, a substituted or unsubstituted $C_1$-$C_6$ alkoxy, a substituted or unsubstituted $C_3$-$C_6$ cycloalkyl, a substituted or unsubstituted $C_6$-$C_{18}$ aryl, a substituted or unsubstituted $C_4$-$C_{10}$ heteroaryl containing one or two heteroatoms selected from N, O and S, or form a substituted or unsubstituted $C_{10}$-$C_{18}$ fused aryl group together with the phenyl group linked therewith;

m, n, p and q each independently represent 0, 1, 2 or 3;

the substituents are one or more groups selected from the group consisting of a $C_1$-$C_6$ alkyl, a $C_1$-$C_6$ alkoxy or a $C_6$-$C_{18}$ aryl.

In another embodiment of the present invention, $[R_1]_m$ and $[R_2]_n$ are identical to $[R_3]_p$ and $[R_4]_q$, respectively; and the substitution positions on the phenyls of $[R_1]_m$ and $[R_2]_n$ are identical to those of $[R_3]_p$ and $[R_4]_q$, respectively.

It can be understood that, since the C—N single bond of the aromatic amine of formula I is rotatable, "$[R_1]_m$ and $[R_2]_n$ are identical to $[R_3]_p$ and $[R_4]_q$, respectively" may also be stated as "$[R_1]_m$ and $[R_2]_n$ are identical to $[R_4]_q$ and $[R_3]_p$, respectively".

In another embodiment of the present invention, $[R_1]_m$, $[R_2]_n$, $[R_3]_p$ and $[R_4]_q$ are the same, and the substitution positions of $[R_1]_m$, $[R_2]_n$, $[R_3]_p$ and $[R_4]_q$ on the phenyls are the same.

In the present application, the same substitution position on the phenyls means that the corresponding substituents are simultaneity at para-, ortho-, or meta-positions with respect to the N atom of the triarylamine groups.

Corresponding to the above aromatic amine derivatives, embodiments of the present invention also provide their preparation method, as shown in FIG. 1, comprising:

101, adding 5,11-disubstituted thieno[3',2':5,6]indolo [3,2-b]thieno[3,2-f]indole (formula II), triarylamine of the formula IT and/or IV, a catalyst, a base, a phase transfer catalyst and a solvent into a reaction vessel and mixing them;

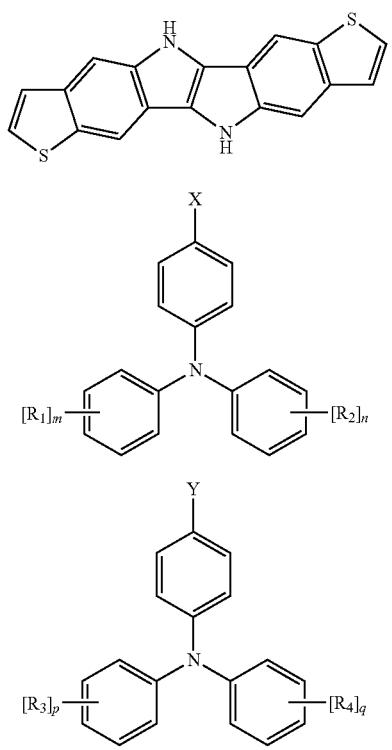

II

III

IV wherein X and Y in triarylamine III and IV each independently represent a halogen, such as F, Cl, Br, I and the like.

5,11-disubstituted thieno[3',2':5,6]indolo [3,2-b]thieno[3, 2-f]indole of the present embodiment can be synthesized through procedures described in the literature Chem. Commun., 2012, 48, 12225-12227, which will not be described again here.

Triarylamine of the formulae III and IV can be synthesized, or some of them can be also obtained commercially. Take a triarylamine of the formula III as an example: it may be obtained by reacting a $[R_1]_m$-substituted aniline with a $[R_2]_n$ substituted bromobenzene to obtain a diphenylamine and then reacting the diphenylamine with p-bromo-iodobenzene, or by directly reacting a commercially available $[R_1]_m$, $[R_2]_n$-substituted diphenylamine with p-bromo-iodobenzene.

Wherein the catalyst, for example, can be copper, copper salt or copper oxide and the like. The base for example can be carbonate or bicarbonate and the like. The phase transfer catalyst for example can be 18-crown-6. The solvent for example can be a mixture of 1,3-dimethyl-3,4,5,6-tetrahydro-2(1H)-pyrimidinone (DMPU) and o-dichlorobenzene. It can be understood that the described above is only exemplificative, which does not limit the protection scope of the present invention.

102, refluxing the obtained mixture under stirring to produce the aromatic amine derivative of the formula I;

A variety of aromatic amine derivatives (for example, those listed in Table 1) can be synthesized by the methods of the present invention.

Optionally, in another embodiment, in step 101, triarylamine of the formula III is the same as triarylamine of the formula IV. Further optionally, the molar ratio of 5,11-disubstituted thieno[3',2':5,6]indolo [3,2-b]thieno[3,2-f]indole (formula II) to triarylamine is from 1:2 to 1:4, preferably from 1:2 to 1:3. Specifically, said molar ratio is 1:2.5, 1:2.7, 1:3.5 and so on. These ratio ranges or proportions can increase the yield of the aromatic amine derivative of the formula I.

It can be understood that, after step 102, an optional refinement step may be included to purify the crude product, e.g., adding o-dichlorobenzene, extracting, washing with water, liquid separating, obtaining the organic phase, drying and rotary evaporating the organic phase to give the refined aromatic amine derivative I.

Figure 2:
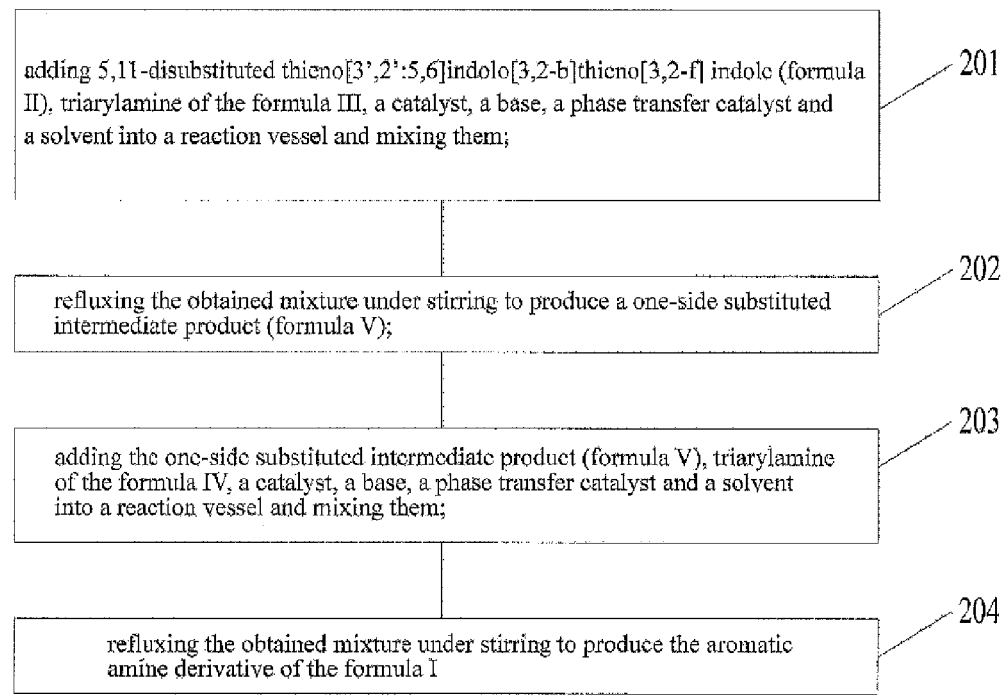
FIG. 2 is a flowchart showing a manufacture process of an aromatic amine derivative provided by another embodiment of the present invention.

In another embodiment provided by the present invention, triarylamine of the formula III is different from triarylamine of the formula IV, then the production method is as shown in FIG. 2, which comprises:

201, adding 5,11-disubstituted thieno[3',2':5,6]indolo [3,2-b]thieno[3,2-f]indole (formula II), triarylamine of the formula III or IV, a catalyst, a base, a phase transfer catalyst and a solvent into a reaction vessel and mixing them;

202, refluxing the obtained mixture under stirring to produce a one-side substituted intermediate product (formula V);

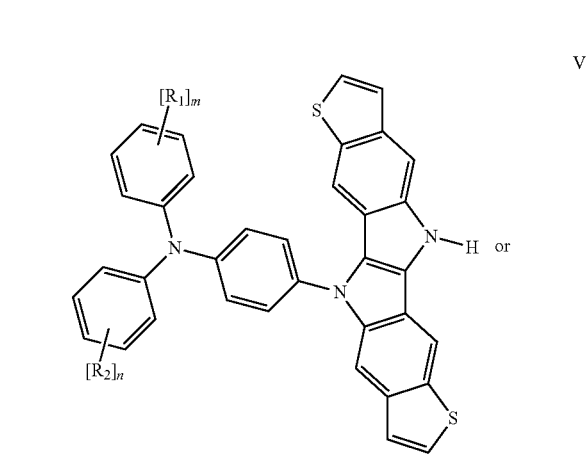

V

-continued

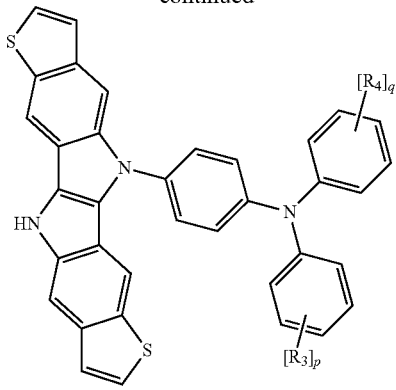

203, adding the one-side substituted intermediate product (formula V), triarylamine of the formula IV or III, a catalyst, a base, a phase transfer catalyst and a solvent into a reaction vessel and mixing them; and 204, refluxing the obtained mixture under stirring to produce the aromatic amine derivative of the formula I.

In a preparation method of the aromatic amine derivative provided by one embodiment of the present invention, in the case of these two triarylamines being different, the two triarylamines are reacted with 5,11-disubstituted thieno[3',2':5,6]indolo [3,2-b]thieno[3,2-f]indole successively, thereby increasing the yield of the final product.

Preferably, in the above embodiment, the molar ratio of 5,11-disubstituted thieno[3',2':5,6]indolo [3,2-b]thieno[3,2-f]indole (formula II) to the triarylamine of the formula III or IV is from 1:1 to 1:2, preferably is from 1:1 to 1:1.5, and more preferably is 1:1.

It is further preferred in the above embodiment that, the molar ratio of the one-side substituted intermediate product (formula V) to the triarylamine of the formula IV or III is from 1:1 to 1:2, preferably is from 1:1 to 1:1.5, and more preferably is 1:1.

One embodiment of the present invention provides a preparation method of an aromatic amine derivative by reacting two different aromatic amines with 5,11-disubstituted thieno[3',2':5,6]indolo [3,2-b]thieno[3,2-f]indole (formula II), wherein the reaction ratio between 5,11-disubstituted thieno[3',2':5,6]indolo [3,2-b]thieno[3,2-f]indole and the triarylamine of the formula III or IV has been reduced to from 1:1 to 1:2 so as to increase the proportion of the one-side substituted intermediate product substituted and reduce the proportion of the both-side substituted intermediate product.

Embodiments of the present invention provide an aromatic amine derivative as a hole transport material.

Embodiments of the present invention also provide an organic electroluminescent device comprising a cathode, at least one light emitting unit and an anode. Said light emitting unit comprises a hole transporting layer comprising an aromatic amine derivative provided by the present invention.

The organic electroluminescent device comprises one or more light emitting units interposed between the anode and the cathode, and each light emitting unit for example may comprise a hole transporting layer, a light emitting layer, an electron transporting layer and an electron injecting layer, and so on. The aromatic amine derivative of formula I provided by the present invention is used as the hole transporting material in the hole transporting layer.

Optionally, said organic electroluminescent devices are phosphorescent devices.

And optionally, a light-emitting layer generally comprises a host material and a light emitting material. The light emitting material may be a phosphorescent dye such as heavy metal (Ir, Pt, Os, Ru, Re, Pd, etc.) complexes, preferably a complex of Ir or Pt, most preferably green phosphorescent dyes $Ir(ppy)_3$ and $Ir(ppy)_2(acac)$, red phosphorescent dye PtOEP, and a blue phosphorescent dye FIrpic. Their formulae are shown below:

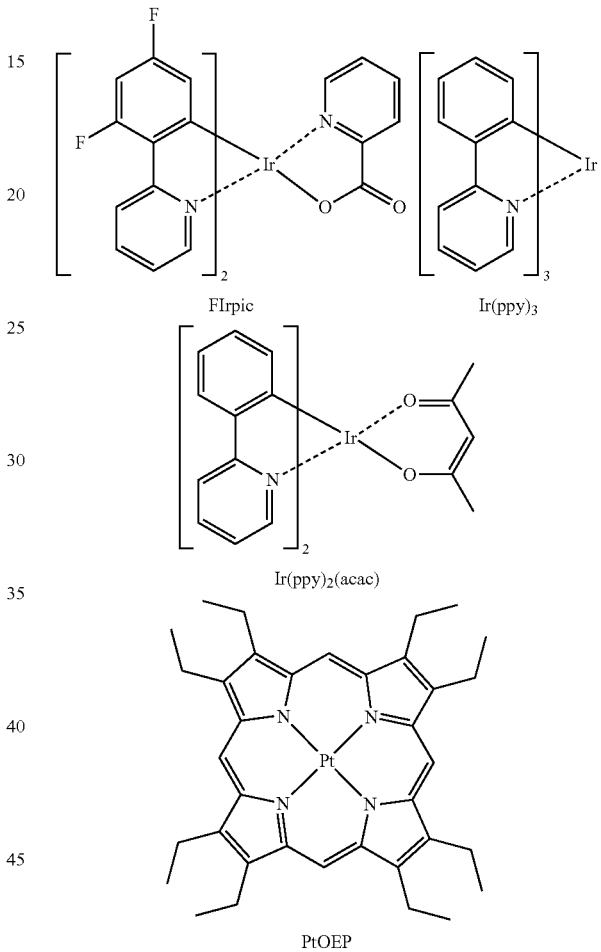

The anode material may be a highly conductive transparent material, such as indium tin oxide (ITO), indium zinc oxide (IZO), tin oxide ($SnO_2$), and zinc oxide (ZnO).

The cathode may be a metal or a mixture thereof, such as Mg:Ag and Ca:Ag, or may has a structure of electron injecting layer/metal layer, such as the common cathode structure LiF/Al, $Li_2O$ and the like.

It should be understood that the above description is only optionally illustrative, but not a limitation to the scope of the present invention.

It is also understood that the organic electroluminescence devices may further include a substrate or the like, such as conventional plastic substrate or glass substrate, which will not be described in detail here.

With the aromatic amine derivative provided by the embodiments of the present invention, the hole transporting layer of the electroluminescent device exhibits good film-forming properties, and is easy to produce. Moreover, since heteroatoms such as N and S have been introduced into the linear π-conjugation system of the molecule, the oxidation and reduction repeatability of the molecule has been insured while the carrier transporting characteristics are maintained, resulting in long life of the organic electroluminescent device.

In order to better illustrate the aromatic amine derivative, its preparation method, uses and organic electroluminescent devices provided by the present invention, specific embodiments will be described below in detail.

Instruments and Equipments

In the present embodiments, mass spectra are determined using ZAB-HS mass spectrometer (Micromass Ltd. UK), and elemental analysis is determined using vario EL elemental analyzer (Elementar Analysensysteme GmbH Co., Ltd. UK).

Preparation of 5,11-disubstituted thieno[3',2':5,6]indolo [3,2-b]thieno [3,2-f]Indole It is synthesized according to the method published in Chem. Commun., 2012, 48, 12225-12227.

The reaction principle is as follows:

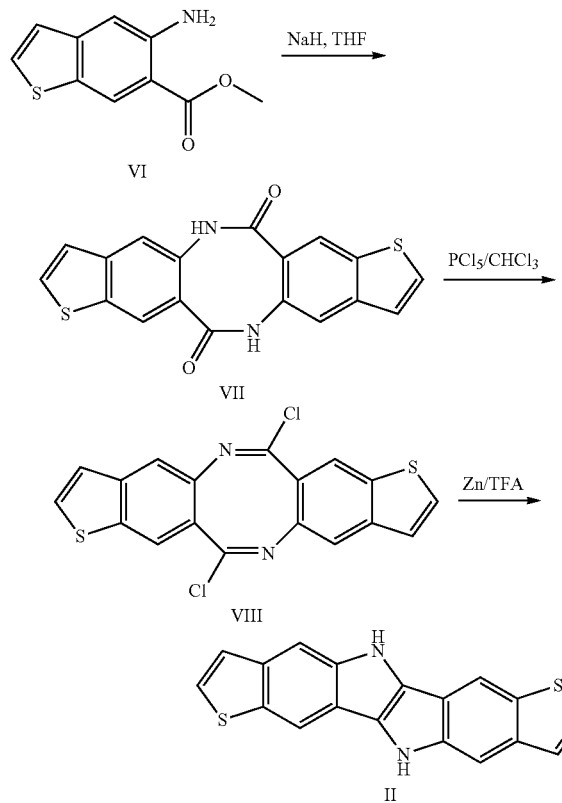

The reaction procedure is as follows:

Preparation of Compound VII: under a nitrogen atmosphere, NaH (6.7 g, 0.2 mol, 72%) and dehydrated THF (150 mL) were added to a 500 mL three-necked round bottom flask. At room temperature, a 150 mL THF solution of 20.7 g (0.1 mol) methyl-5-amino-benzo[b]thiophene-6-carboxylic acid of the formula VI was slowly added dropwise. The mixture was heated at reflux under magnetic stirring for 3 days, and then cooled to room temperature. After that, the mixture was slowly poured into 500 mL 0.1 mol/L hydrochloric acid solution in ice water. A large amount of precipitate emerged. The precipitate was filtered, washed and dried to give a crude product. A light yellow crystalline product (11.5 g) was obtained through purification by recrystallization, yield: 65.6%.

Preparation of Compound VIII: The resultant compound VII (10.5 g, 0.03 mol) and $PCl_5$ (12.5 g, 0.06 mol) were mixed in 150 mL of chloroform, heated at reflux for 6 hours, cooled and filtered to give the product. A light yellow crystal (6.1 g) was obtained through purification by recrystallization, yield: 52.5%.

Preparation of Compound II: The resulting compound VIII 5.8 g (0.015 mol) was dissolved in 100 mL dehydrated THF. Activated zinc (Zn) 11.8 g (0.18 mol) was added in batches, and then trifluoroacetic acid (TFA) 41 g (0.36 mol) was slowly added under magnetic stirring. Stirring continues for 10 hours at room temperature. $NH_4Cl$ solution was added to quench the reaction. Ethyl acetate was added for extraction, and the organic phase was dried over anhydrous $MgSO_4$. The organic solvent was removed by rotary evaporation to give the crude product. 3.52 g compound II was obtained through recrystallization from ethanol, yield. 73.79%.

Compound II MS (m/z): 854; Elemental analysis ($C_{58}H_{38}N_4S_2$): Theory C, 81.47% H, 4.48%, and N, 6.56%. Found C, 81.39%, H, 4.45%, and N, 6.52%.

Preparation of the Aromatic Amine Derivative

1. Preparation of Compound I-1

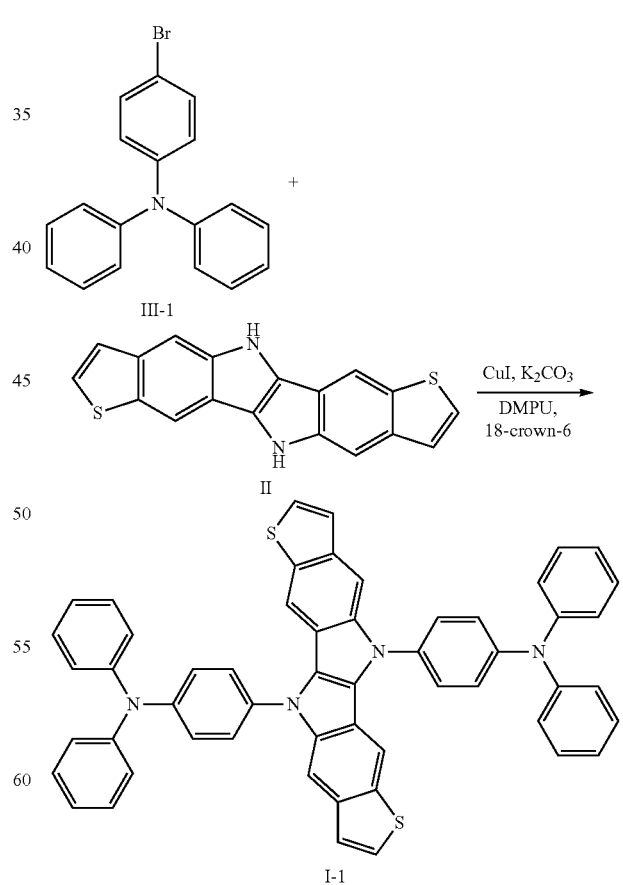

Under nitrogen atmosphere, to a 250 mL three-necked round bottom flask was added 15.9 g (0.05 mol) compound II, 32.3 g (0.10 mol) 4-bromo-triphenylamine, 0.2 g (2 mol %) CuI, 20.7 g (0.15 mol) K$_2$CO$_3$, 0.8 g (6 mol %) 18-crown-6, 5 mL 1,3-dimethyl-3,4,5,6-tetrahydro-2(1H)-pyrimidinone (DMPU) and 50 mL o-dichlorobenzene. After reflux for 18 h under magnetic stirring, the mixture was cooled. 200 mL CH$_2$Cl$_2$ was added, and the mixture was washed with an appropriate amount of water for 2-3 times. After liquid separation, the organic phase was dried over anhydrous MgSO$_4$. The organic solvent was removed by rotary evaporation to give a crude product. The crude product was purified by silica gel (200-300 mesh) column chromatography to give 29.1 g product, yield: 72.4%.

Compound I-1 MS (m/z): 804; Elemental analysis (C$_{54}$H$_{36}$N$_4$S$_2$): Theory C, 80.57%, H, 4.51%, N, 6.96%. Found C, 80.33%, H, 4.45%, N, 6.87%.

2. Preparation of Compound I-4

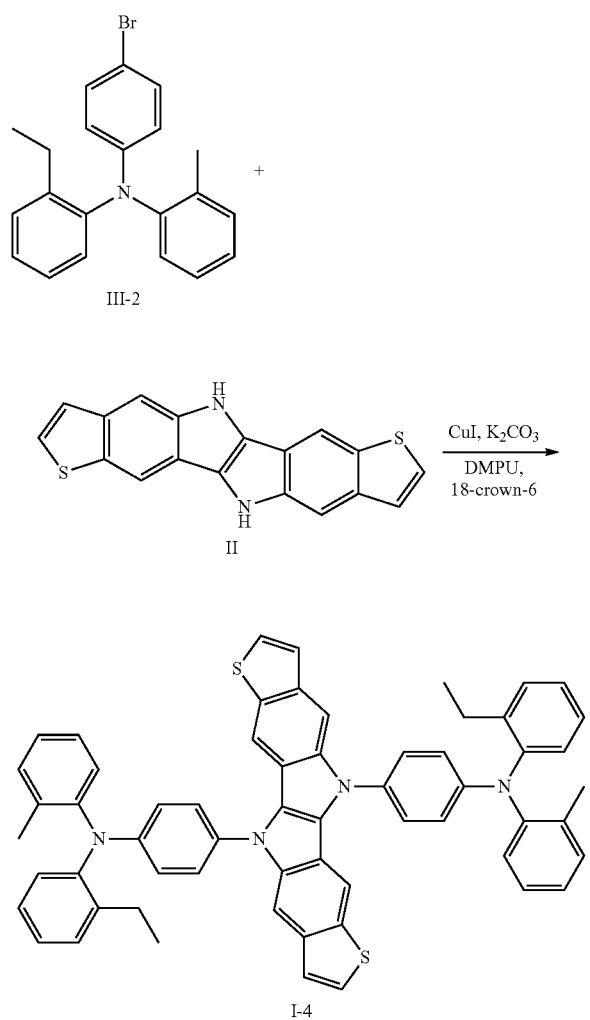

Compound of formula I-4 was prepared through similar procedures as those of Compound I-1, except that N-(4-bromophenyl)-2-ethyl (o-tolyl) aniline III-2 was used instead of 4-bromo-triphenylamine III-1. Yield: 71.53%.

Compound I-4 MS (m/z): 888; Elemental analysis (C$_{60}$H$_{48}$N$_4$S$_2$): Theory C, 81.05%, H, 5.44%, N, 6.30%. Found C, 81.00%, H, 5.36%, N, 6.22%.

3. Preparation of Compound I-6

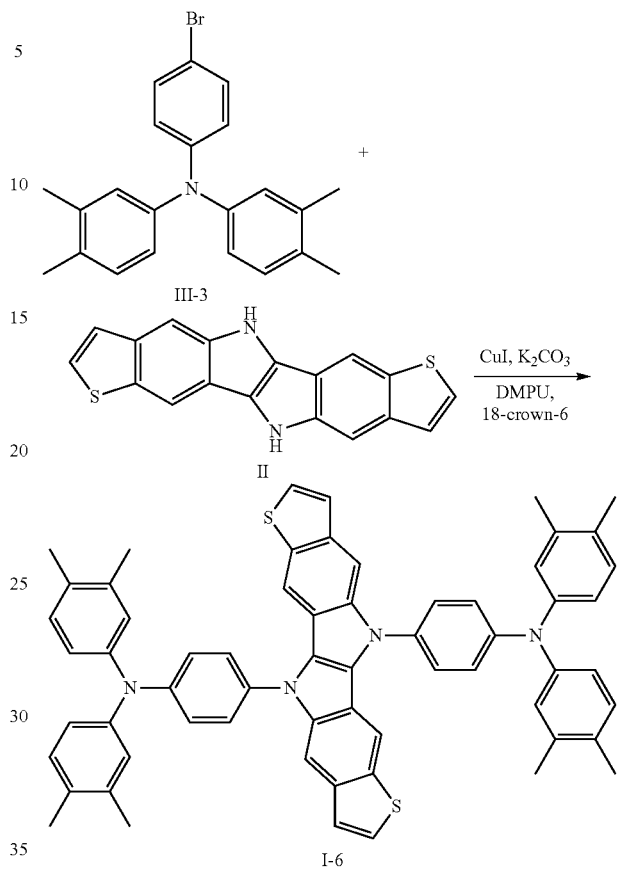

Compound of formula I-6 was prepared through similar procedures as those of Compound I-1, except that N-(4-bromophenyl)-(3,4-dimethylphenyl)-3,4-dimethylaniline III-3 was used instead of 4-bromo-triphenylamine III-1. Yield: 70.22%.

Compound I-6 MS (m/z): 916; Elemental analysis (C$_{62}$H$_{52}$N$_4$S$_2$): Theory C, 81.19%, H, 5.71%, N, 6.11%. Found C, 81.26%, H, 5.66%, N, 6.14%.

4. Preparation of Compound I-9

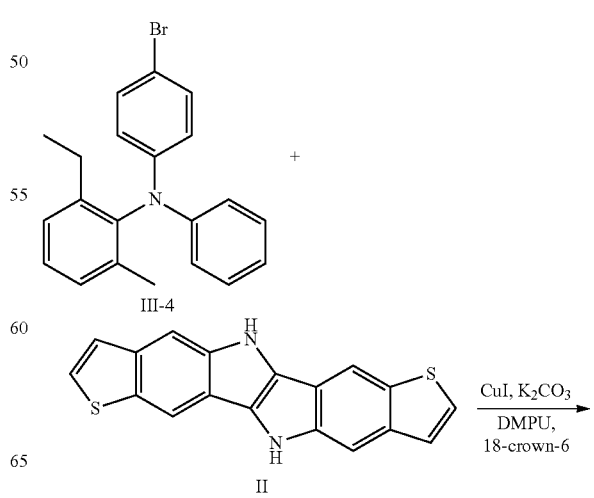

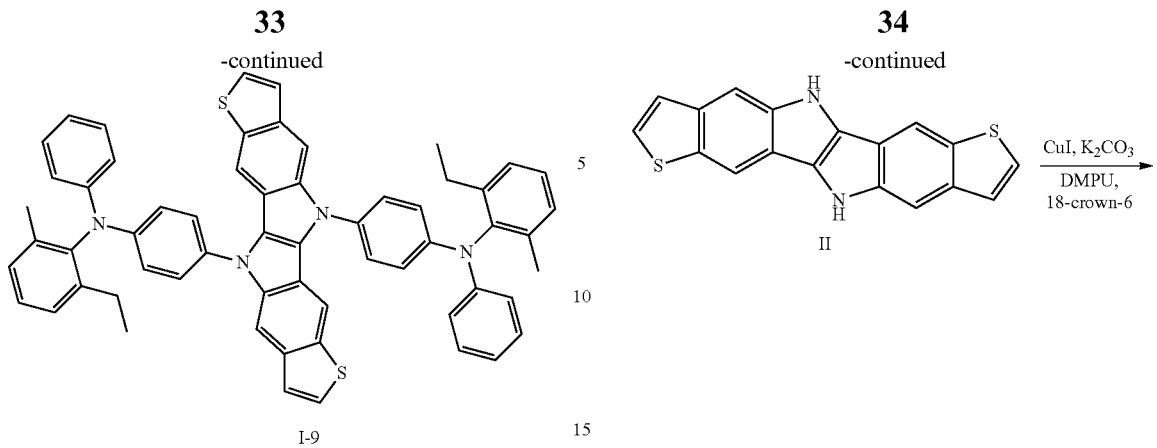

I-9

Compound of formula I-9 was prepared through similar procedures as those of Compound I-1, except that N-(4-bromophenyl)-N-(2-ethyl-6-methyl-phenyl) aniline 11-4 was used instead of 4-bromo-triphenylamine III-1. Yield: 65.16%.

Compound I-9 MS (m/z): 888; Elemental analysis ($C_{60}H_{48}N_4S_2$): Theory C, 81.05%, H, 5.44%, N, 6.30%. Found C, 81.00%, H, 5.51%, N, 6.24%.

5. Preparation of Compound I-11

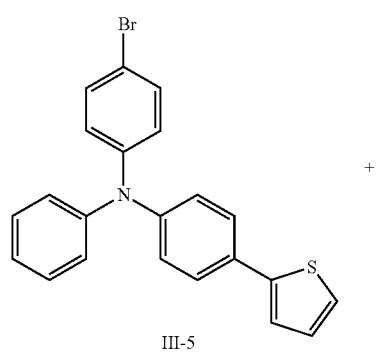

III-5

I-11

Compound of formula I-11 was prepared through similar procedures as those of Compound I-1, except that N-(4-bromo-phenyl)-N-(4-(2-thienyl)phenyl) aniline III-5 was used instead of 4-bromo-triphenylamine III-1. Yield: 69.65%.

Compound I-11 MS (m/z): 968; Elemental analysis ($C_{62}H_{40}N_4S_4$): Theory C, 76.86%, H, 4.16%, N, 5.78%. Found C, 76.80%, H, 4.11%, N, 5.80%.

6. Preparation of Compound I-14

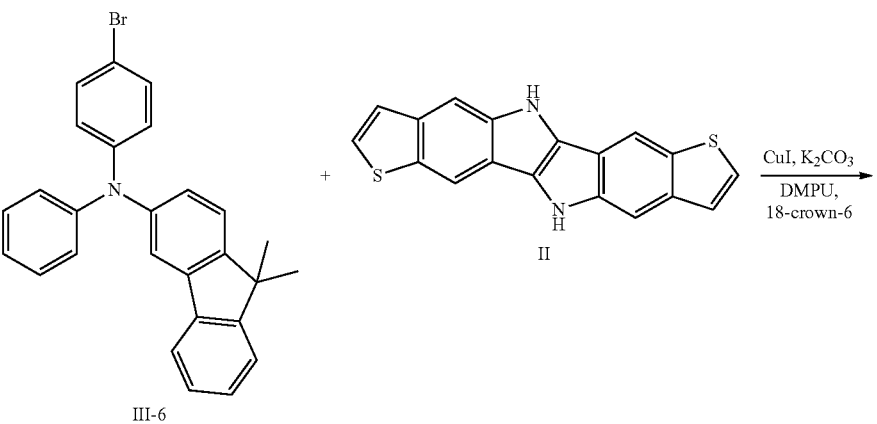

III-6

II

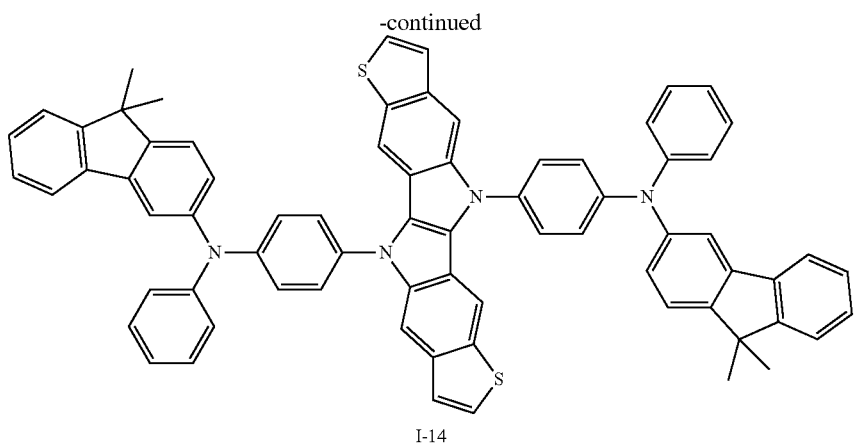

I-14

Compound of formula I-14 was prepared through similar procedures as those of Compound I-1, except that N-phenyl-N-(4-bromophenyl)-9,9-dimethyl-fluorenyl-3-amine III-6 was used instead of 4-bromo-triphenylamine III-1. Yield: 55.80%.

Compound I-14 MS (m/z): 1036; Elemental analysis ($C_{72}H_{52}N_4S_2$): Theory C, 83.36%, H, 5.05%, N, 5.40%. Found C, 83.29%, H, 5.00%, N, 5.44%.

7. Preparation of Compound I-16

Compound of formula I-16 was prepared through similar procedures as those of Compound I-1, except that N-(4-bromophenyl)-N,9-diphenyl-carbazol-3-amine 11-7 was used instead of 4-bromo-triphenylamine III-1. Yield: 62.34%.

Compound I-16 MS (m/z): 1134; Elemental analysis ($C_{78}H_{50}N_6S_2$): Theory C, 82.51%, H, 4.44%, N, 7.40%. Found C, 82.43%, H, 4.38%, N, 7.35%.

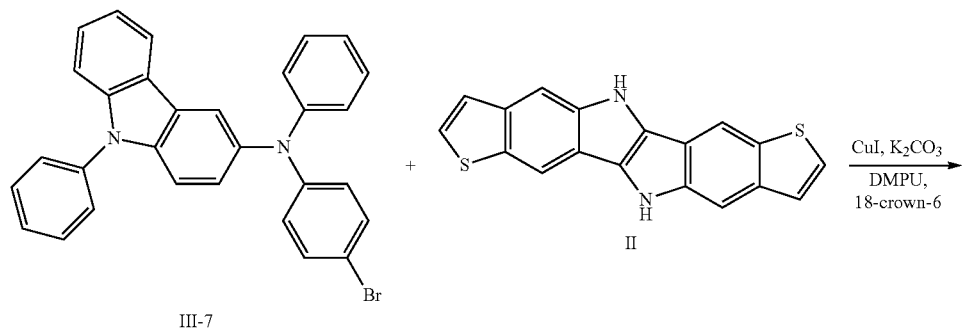

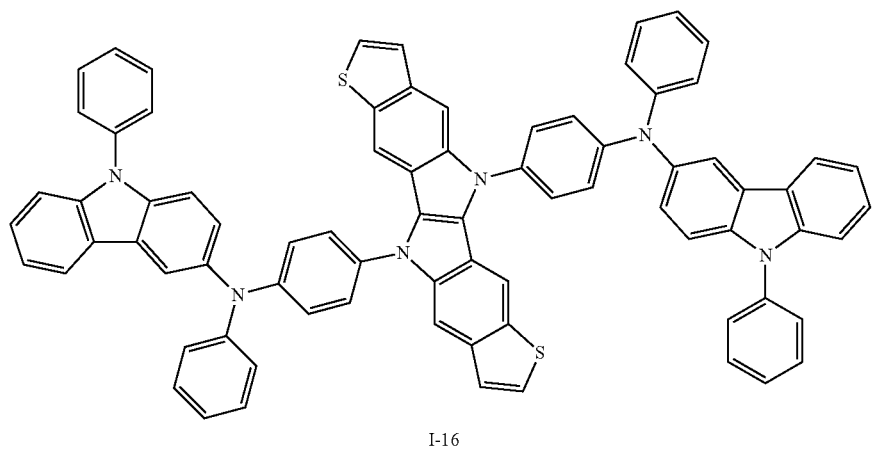

I-16

8. Preparation of Compound I-19
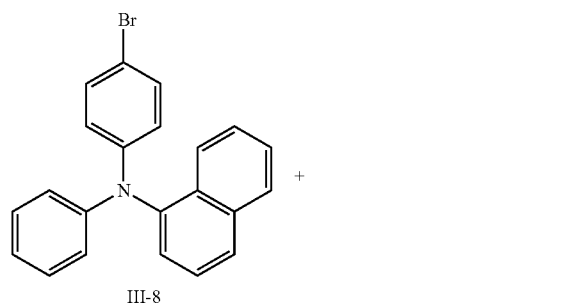
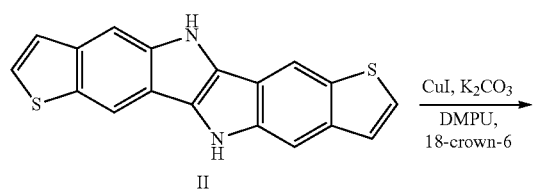
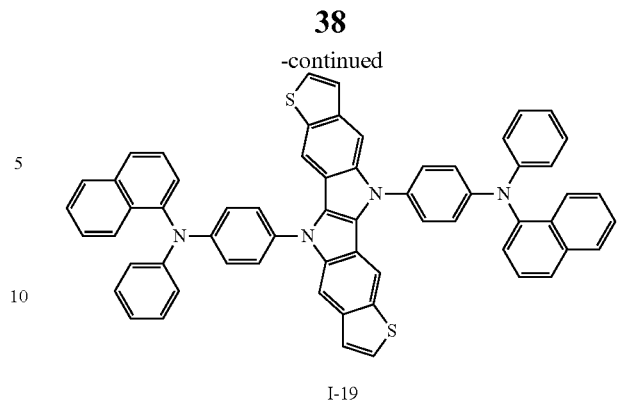
Compound of formula I-19 was prepared through similar procedures as those of Compound I-1, except that N-(4-bromophenyl)-N-phenyl-1-naphthylamine III-8 was used instead of 4-bromo-triphenylamine III-1. Yield: 52.43%.
Compound I-19 MS (m/z): 904; Elemental analysis ($C_{62}H_{40}N_4S_2$): Theory C, 82.27%, H, 4.45%, N, 6.19%. Found C, 82.22%, H, 4.39%, N, 6.26%.
9. Preparation of Compound I-23
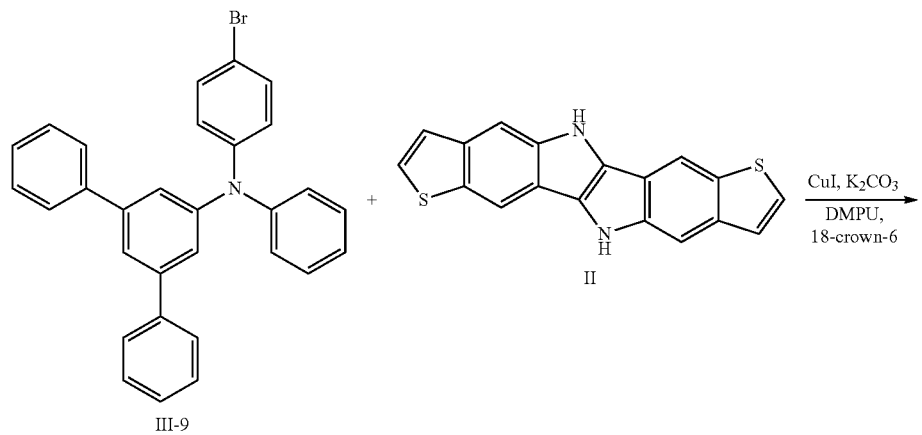
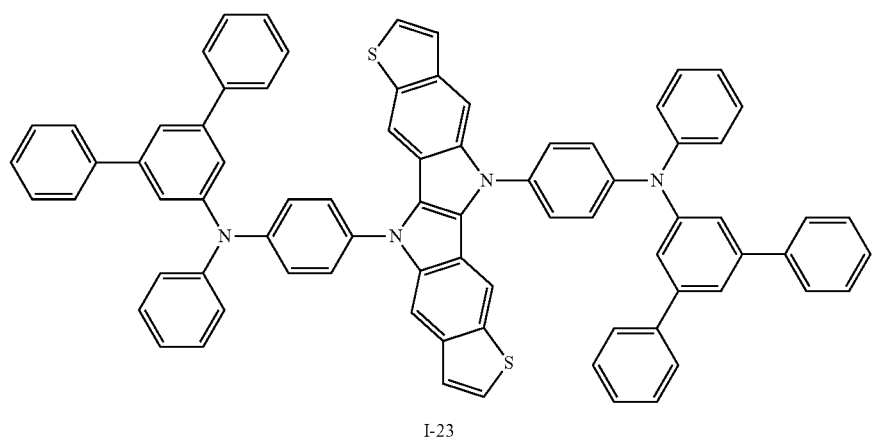

Compound of formula I-23 was prepared through similar procedures as those of Compound I-1, except that N-(4-bromophenyl)-N-phenyl-[1,1':3',1''-terphenyl]-5'-amine III-9 was used instead of 4-bromo-triphenylamine III-1. Yield: 49.65%.

Compound I-23 MS (m/z): 1108; Elemental analysis ($C_{78}H_{52}N_4S_2$): Theory C, 84.44%, H, 4.72%, N, 5.05%. Found C, 84.38%, H, 4.66%, N, 5.12%.

10. Preparation of Compound I-28

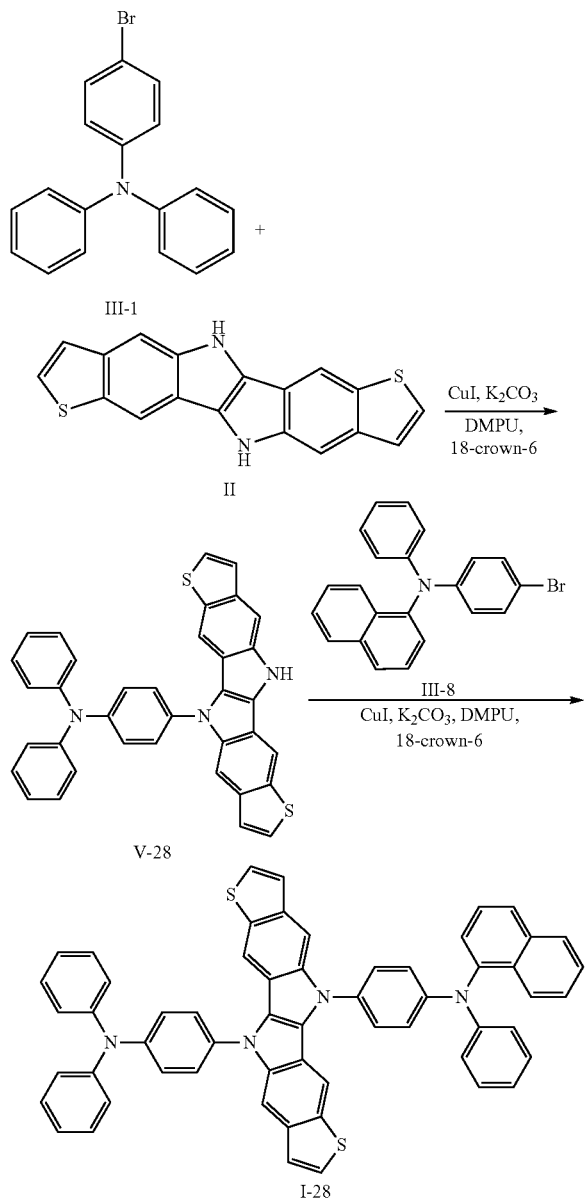

Preparation of Compound V-28: Under a nitrogen atmosphere, to a 250 mL three-necked round bottom flask was added 15.9 g (0.05 mol) compound II, 16.2 g (0.05 mol) 4-bromo triphenylamine, 0.15 g (1.5 mol %) CuI, 16.6 g (0.12 mol) $K_2CO_3$, 0.6 g (4.5 mol %) 18-crown-6, 5 mL 1,3-dimethyl-3,4,5,6-tetrahydro-2(1H)-pyrimidinone (DMPU) and 50 mL o-dichlorobenzene. After reflux for 10 h under magnetic stirring, the mixture was cooled. 150 mL $CH_2Cl_2$ was added, and the mixture was washed with an appropriate amount of water for 2-3 times. After liquid separation, the organic phase was dried over anhydrous $MgSO_4$. The organic solvent was removed by rotary evaporation to give a crude product. The crude product was purified by silica gel (200-300 mesh) column chromatography to give 19.3 g product, yield: 68.8%.

Preparation of Compound I-28: Refer to the preparation of V-28, under nitrogen atmosphere, to a 250 mL three-necked round bottom flask was added 16.9 g (0.03 mol) compound V-28, 11.2 g (0.03 mol) N-(4-bromophenyl)-N-phenyl-1-naphthylamine, 0.1 g (1.0 mol %) CuI, 13.8 g (0.10 mol) $K_2CO_3$, 0.48 g (3.6 mol %) 18-crown-6, 4 mL 1,3-dimethyl-3,4,5,6-tetrahydro-2(1H)-pyrimidinone (DMPU) and 40 mL o-dichlorobenzene. Purification was carried out after the reaction to obtain 18.3 g products, yield 71.34%.

Compound I-28 MS (m/z): 854; Elemental analysis ($C_{58}H_{38}N_4S_2$): Theory C, 81.47%, H, 4.48%, N, 6.56%. Found C, 81.39%, H, 4.45%, N, 6.52%.

According to the preparation method of the present invention, the others of compounds I-1 to I-30 were also prepared similar to the foregoing specific embodiments, and listed in Table 2.

TABLE 2

| Compound No. | Product MS (m/z) | Molecular Formula | Molecular Weight | Yield % |
|---|---|---|---|---|
| I-2 | 860 | $C_{58}H_{44}N_4S_2$ | 861.13 | 68.52 |
| I-3 | 956 | $C_{66}H_{44}N_4S_2$ | 957.21 | 70.69 |
| I-5 | 972 | $C_{66}H_{60}N_4S_2$ | 973.34 | 1.22 |
| I-7 | 944 | $C_{64}H_56N_4S_2$ | 945.29 | 68.54 |
| I-8 | 860 | $C_{58}H_{44}N_4S_2$ | 861.13 | 69.63 |
| I-10 | 944 | $C_{64}H_{56}N_4S_2$ | 945.29 | 72.39 |
| I-12 | 1052 | $C_{74}H_{44}N_4S_2$ | 1053.30 | 65.43 |
| I-13 | 936 | $C_{60}H_{40}N_8S_2$ | 937.14 | 66.58 |
| I-15 | 1004 | $C_{70}H_{44}N_4S_2$ | 1005.26 | 62.74 |
| I-17 | 924 | $C_{58}H_{44}N_4O_4S_2$ | 925.12 | 70.17 |
| I-18 | 904 | $C_{62}H_{40}N_4S_2$ | 905.14 | 63.95 |
| I-20 | 1004 | $C_{70}H_{44}N_4S_2$ | 1005.26 | 58.33 |
| I-21 | 1004 | $C_{70}H_{44}N_4S_2$ | 1005.26 | 57.86 |
| I-22 | 1108 | $C_{78}H_{52}N_4S_2$ | 1109.40 | 50.23 |
| I-24 | 1132 | $C_{78}H_{76}N_4S_2$ | 1133.59 | 60.12 |
| I-25 | 1004 | $C_{70}H_{44}N_4S_2$ | 1005.26 | 54.33 |
| I-26 | 1056 | $C_{74}H_{48}N_4S_2$ | 1057.33 | 55.87 |
| I-27 | 1134 | $C_{78}H_{50}N_6S_2$ | 1135.40 | 56.21 |
| I-29 | 896.3 | $C_{61}H_{44}N_4S_2$ | 897.16 | 70.29 |
| I-30 | 888 | $C_{60}H_{48}N_4S_2$ | 889.18 | 88.35 |

Preparation of Triarylamine

The reactant triarylamine used in the preparation of the aforementioned aromatic amine derivatives can be synthesized according to the following examples.

1. Preparation of Compound III-2

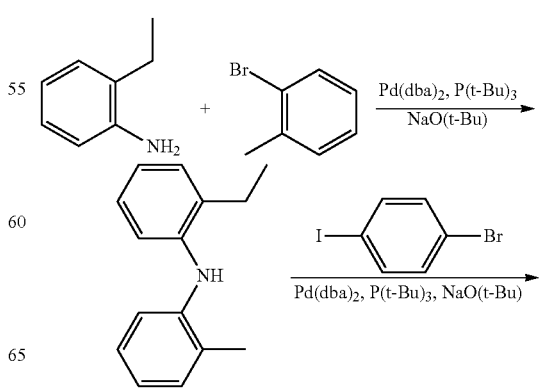

-continued

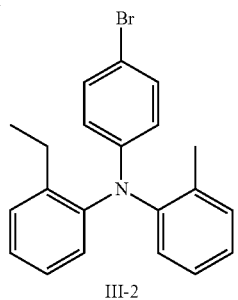

III-2

Preparation of N-(2-ethylphenyl)-2-methylaniline: under nitrogen atmosphere, to a 500 ml three-necked round bottom flask was added 6.05 g (0.05 mol) 2-methyl bromobenzene, 10.20 g (0.06 mol) of 2-ethyl aniline, 0.14 g (0.5 mol %) Pd(dba)$_2$, 0.5 ml (0.5 mol %) 10% P(t-Bu)$_3$ solution in cyclohexane and 4.80 g (0.05 mol) NaO(t-Bu), followed by addition of 260 ml dehydrated toluene to obtain a reaction solution. The reaction was stirred magnetically at 110° C. in an oil bath at reflux for 3 h, cooled, and then washed with an appropriate amount of water for 2-3 times. The reaction solution was separated, and the resulting organic phase was dried over anhydrous MgSO$_4$. The organic solvent was removed by rotary evaporation to give a crude product. The crude product is recrystallized from petroleum ether-ethanol to give 8.88 g white crystals, yield 84.2%.

Synthesis of Compound III-2: refer to the preparation of N-(2-ethylphenyl)-2-methyl aniline, under nitrogen atmosphere, reacting N-(2-ethylphenyl)-2-methylaniline with 1-bromo-4-iodobenzene to obtain pale yellow crystals III-2, yield 78.3%.

2. Preparation of Compound III-3

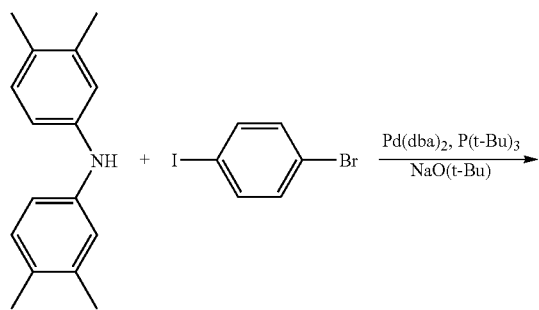

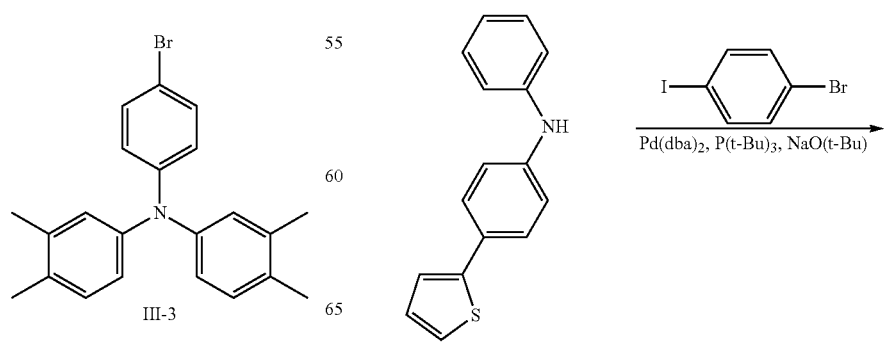

Compound of formula III-3 was prepared through similar procedures as those of Compound III-2, except that bis(3,4-dimethylphenyl) aniline was used instead of N-(2-ethylphenyl)-2-methylaniline.

3. Preparation of Compound III-4

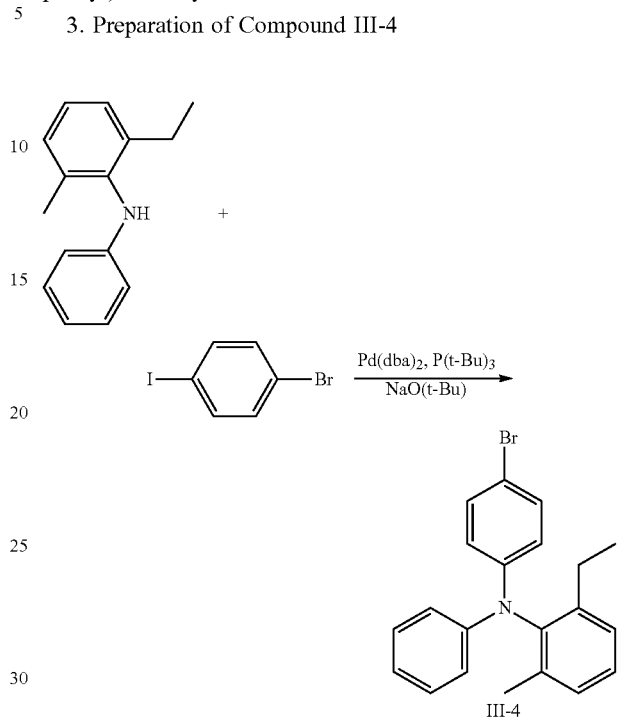

Compound of formula III-4 was prepared through similar procedures as those of Compound III-2, except that N-(2-ethyl-6-methylphenyl) aniline was used instead of N-(2-ethylphenyl)-2-methylaniline.

4. Preparation of Compound III-5

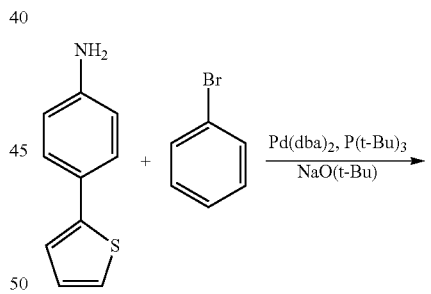

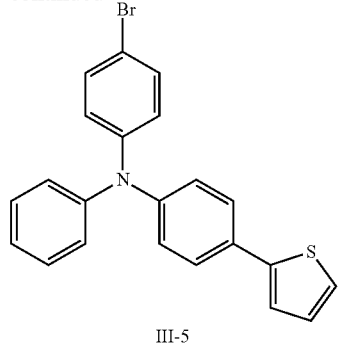

III-5

Compound of formula III-5 was prepared through similar procedures as those of Compound III-2, except that 4-(2-thienyl) aniline and bromobenzene were used instead of 2-ethyl aniline and 2-methyl bromobenzene.

5. Preparation of Compound III-6

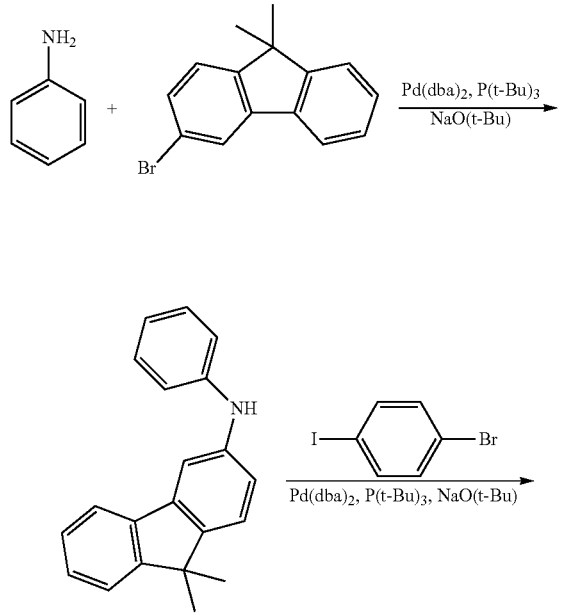

III-6

Compound of formula III-6 was prepared through similar procedures as those of Compound III-2, except that aniline and 3-bromo-9,9-dimethyl-9H-fluorene were used instead of 2-ethyl aniline and of 2-methyl bromobenzene.

6. Preparation of Compound III-7

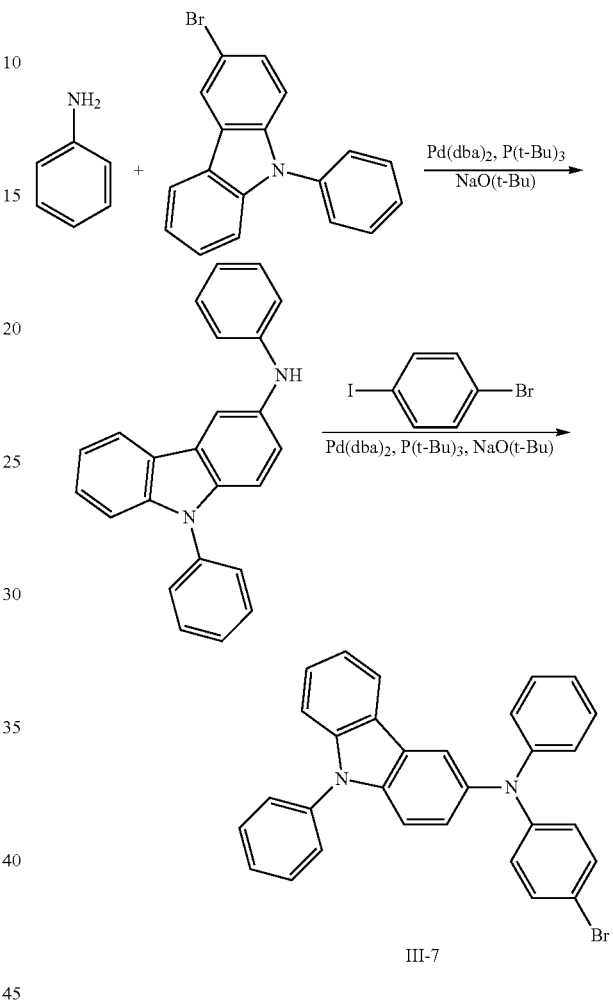

III-7

Compound of formula I-7 was prepared through similar procedures as those of Compound III-2, except that aniline and 3-bromo-9-phenyl-9H-carbazole were used instead of 2-ethyl aniline and 2-methyl bromobenzene.

7. Preparation of Compound III-8

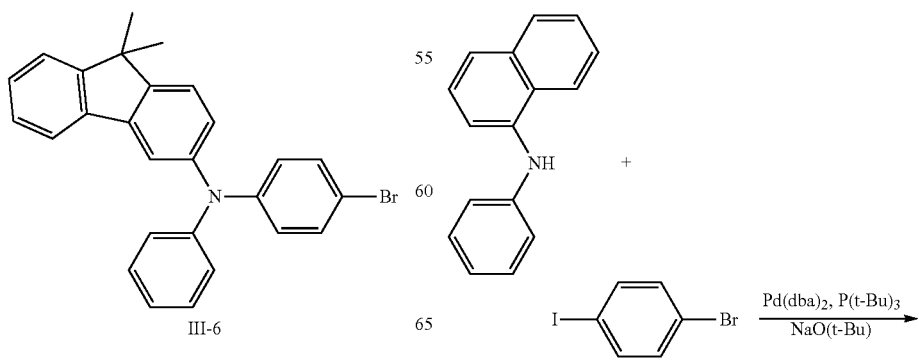

-continued

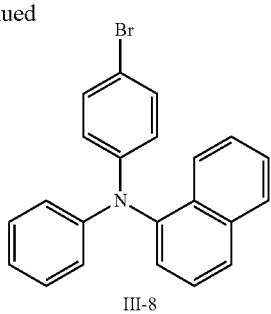

III-8

Compound of formula III-8 was prepared through similar procedures as those of Compound III-2, except that N-phenyl-1-naphthylamine was used instead of N-(2-ethylphenyl)-2-methyl-aniline.

8. Preparation of Compound III-9

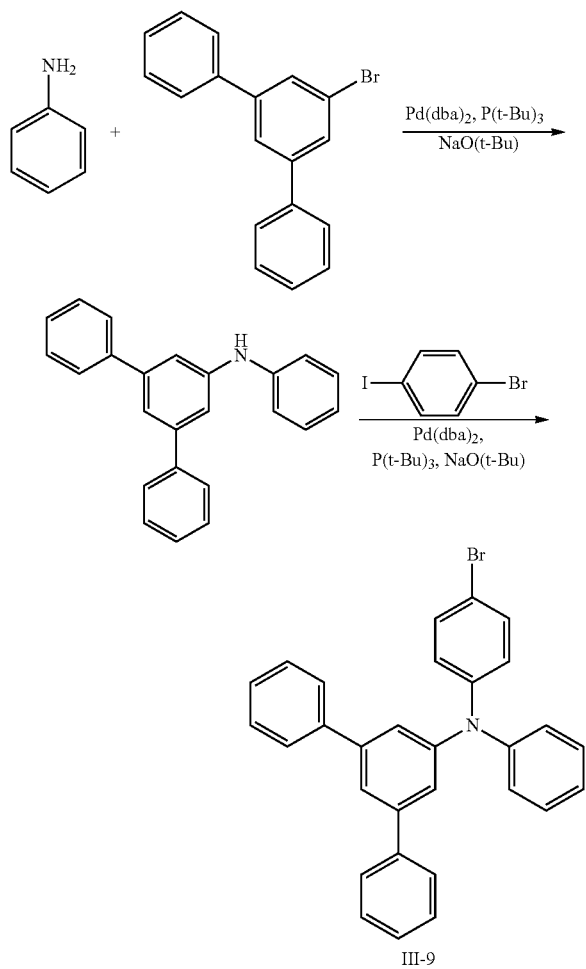

III-9

The Manufacture of Organic Electroluminescent Devices

The aromatic amine derivatives synthesized in the above embodiment were used as the hole transporting materials to prepare organic electroluminescent devices, the procedure is as follows.

Indium tin oxide layer was formed on a glass substrate as a transparent anode. 40 nm of a hole transporting material NPB (Comparative Example) or compound I of the present invention (Example) were deposited through a vacuum deposition method as a hole transporting layer, respectively. The light emitting layer was CBP and 6% blue phosphorescent dye Firpic. 25 nm Bphe was deposited in vacuum on the light emitting layer as an electron transporting layer. 0.5 nm LiF was deposited in vacuum on the electron-transporting layer as an electron injecting layer. 100 nm Al was deposited in vacuum on the electron injecting layer as a cathode.

7 organic electroluminescent devices of the present invention (i.e., Examples 1-7) and a conventional organic electroluminescent device (i.e., Comparative Example 1) were prepared according to the above procedures. Their structures were as follows, in order of anode/hole transporting layer/light emitting layer/electron transporting layer/electron injecting layer/cathode.

COMPARATIVE EXAMPLE 1

ITO/NPB (40 nm)/CBP: 6% Firpic (30 nm)/Bphen (25 nm)/LiF (0.5 nm)/Al (100 nm)

EXAMPLE 1

ITO/I-1 (40 nm)/CBP: 6% (Firpic (30 nm)/Bphen (25 nm)/LiF (0.5 nm)/Al (100 nm)

EXAMPLE 2

ITO/I-9 (40 nm)/CBP: 6% Firpic (30 nm)/Bphen (25 nm)/LiF (0.5 nm)/Al (100 nm)

EXAMPLE 3

ITO/1-9 (40 nm)/CBP: 6% Firpic (30 nm)/Bphen (25 nm)/LiF (0.5 nm)/Al (100 nm)

EXAMPLE 4

ITO/1-19 (40 nm)/CBP: 6% Firpic (30 nm)/Bphen (25 nm)/LiF (0.5 nm)/Al (100 nm)

EXAMPLE 5

ITO/1-27 (40 nm)/CBP: 6% Firpic (30 nm)/Bphen (25 nm)/LiF (0.5 nm)/Al (100 nm)

EXAMPLE 6

ITO/1-28 (40 nm)/CBP: 6% Firpic (30 nm)/Bphen (25 nm)/LiF (0.5 nm)/Al (100 nm)

EXAMPLE 7

ITO/1-30 (40 nm)/CBP: 6% Firpic (30 nm)/Bphen (25 nm)/LiF (0.5 nm)/Al (100 nm)

The properties of Comparative Example 1 and Examples 1-7 are listed in Table 3.

TABLE 3

| Device | Luminance cd/m$^2$ | Current Efficiency cd/A | color coordinates (x, y) | Life (LT$_{50}$, hrs) |
|---|---|---|---|---|
| Comparative Example 1 | 1000 | 5.26 | (0.152, 0.298) | 1000 |
| Example 1 | 1000 | 5.88 | (0.148, 0.309) | 1400 |
| Example 2 | 1000 | 6.22 | (0.150, 0.304) | 1600 |
| Example 3 | 1000 | 5.39 | (0.126, 0.279) | 1200 |
| Example 4 | 1000 | 5.55 | (0.150, 0.288) | 1750 |

TABLE 3-continued

| Device | Luminance cd/m$^2$ | Current Efficiency cd/A | color coordinates (x, y) | Life (LT$_{50}$, hrs) |
|---|---|---|---|---|
| Example 5 | 1000 | 6.03 | (0.141, 0.265) | 1540 |
| Example 6 | 1000 | 6.59 | (0.148, 0.315) | 1300 |
| Example 7 | 1000 | 5.96 | (0.139, 0.288) | 1200 |

As shown in Table 3, compared with the prior art, the organic electroluminescent devices employing the aromatic amine derivatives of Examples of the present invention exhibited an increase in current efficiency and life, which verified beneficial effects of the present invention.

The description set forth above merely refers to the specific embodiments of the disclosure, and is not intended to limit the scope of the present invention. Modifications or variations that those skilled in the art can easily conceive of should be within the scope of the present invention. Therefore, the scope of the present invention should be construed according to the claims.

The present application claims the benefits of the Chinese Application No. 201410169185.9 filed on Apr. 24, 2014, the entire disclosure of which is incorporated herein by reference.

The invention claimed is:

1. An aromatic amine derivative, having a structure of the following general formula I:

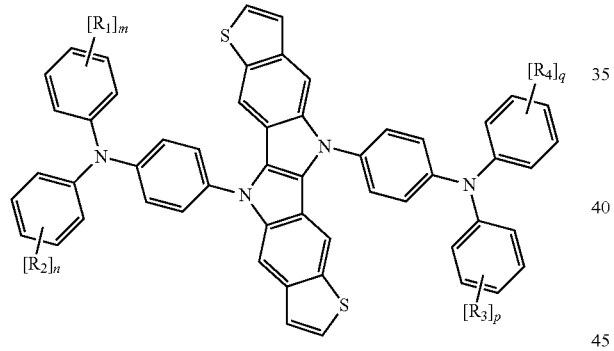

I in which, $R_1$, $R_2$, $R_3$ and $R_4$ each independently represent a substituted or unsubstituted $C_1$-$C_{40}$ alkyl, a substituted or unsubstituted $C_1$-$C_{40}$ alkoxy, a substituted or unsubstituted $C_3$-$C_{40}$ cycloalkyl, a substituted or unsubstituted $C_6$-$C_{50}$ aryl group, a substituted or unsubstituted $C_3$-$C_{50}$ heteroaryl containing one or two heteroatoms selected from N, O and S, or a substituted or unsubstituted $C_{10}$-$C_{40}$ fused aryl grou formed together with the phenyl group linked therewith;

wherein, m, n, p and q each independently represent 0, 1, 2, 3, 4 or 5; and the substituents are one or more groups selected from the group consisting of a halogen, a $C_1$-$C_{10}$ alkyl, a $C_1$-$C_{10}$ alkoxy, a $C_3$-$C_{20}$ cycloalkyl, a $C_6$-$C_{20}$ aryl group or a $C_4$-$C_{20}$ heteroaryl group.

2. The aromatic amine derivative according to claim 1, wherein, $R_1$, $R_2$, $R_3$ and $R_4$ each independently represent a substituted or unsubstituted $C_1$-$C_6$ alkyl, a substituted or unsubstituted $C_1$-$C_6$ alkoxy, a substituted or unsubstituted $C_3$-$C_6$ cycloalkyl, a substituted or unsubstituted $C_6$-$C_{18}$ aryl group, a substituted or unsubstituted $C_4$-$C_{10}$ heteroaryl containing one or two heteroatoms selected from N, O and S, or a substituted or unsubstituted $C_{10}$-$C_{18}$ fused aryl grou formed together with the phenyl group linked therewith;

m, n, p and q each independently represent 0, 1, 2 or 3; and the substituents are one or more groups selected from the group consisting of a $C_1$-$C_6$ alkyl, a $C_1$-$C_6$ alkoxy or a $C_6$-$C_{18}$ aryl group.

3. The aromatic amine derivative according to claim 1, wherein, $[R_1]_m$ and $[R_2]_n$ are identical to $[R_3]_p$ and $[R_4]_q$, respectively; and the substitution positions of $[R_1]_m$ and $[R_2]_n$ on the phenyls are identical to those of $[R_3]_p$ and $[R_4]_q$, respectively.

4. The aromatic amine derivative according to claim 1, wherein, $[R_1]_m$, $[R_2]_n$, $[R_3]_p$ and $[R_4]_q$ are the same, and the substitution positions of $[R_1]_m$, $[R_2]_n$, $[R_3]_p$ and $[R_4]_q$ on the phenyls are the same.

5. A preparation method of the aromatic amine derivative according to claim 1, comprising:

adding 5,11-disubstituted thieno[3',2':5,6] indolo [3,2-b] thieno [3,2-f] indole (formula II), triarylamine of the formula III and/or IV, a catalyst, a base and a solvent into a reaction vessel and mixing them; and

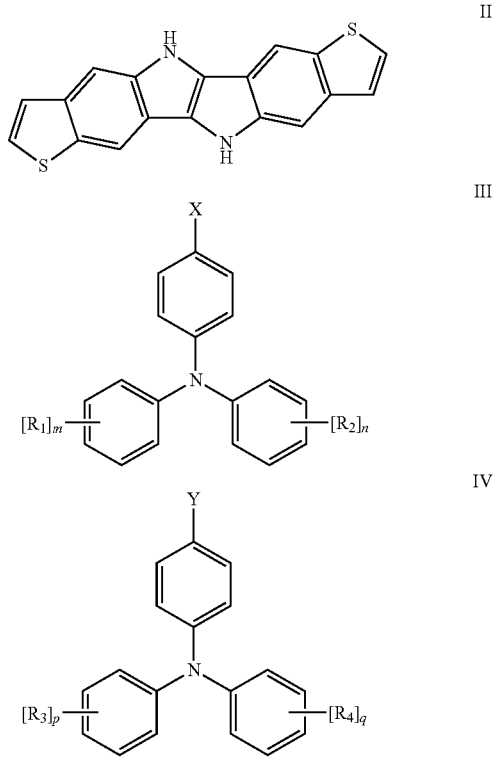

II

III

IV refluxing the obtained mixture under stirring to produce the aromatic amine derivative of the formula I, wherein, X and Y independently represent a halogen; and $R_1$, $R_2$, $R_3$, $R_4$, m, n, p and q are defined as in claim 1.

6. The preparation method according to claim 5, wherein, the triarylamine of formula III is identical to the triarylamine of formula IV.

7. The preparation method according to claim 6, wherein, the molar ratio of 5,11-disubstituted thieno[3',2':5,6] indolo [3,2-b]thieno [3,2-f] indole (formula II) to the triarylamine is from 1:2 to 1:4.

8. The preparation method according to claim 5, wherein the method comprises the following steps when the triarylamine of formula III is different from the triarylamine of formula IV:
adding 5,11-disubstituted thieno[3',2':5,6] indolo [3,2-b] thieno [3,2-f] indole (formula II), triarylamine of the formula III or IV, a catalyst, a base and a solvent into a reaction vessel and mixing them;
refluxing the obtained mixture under stirring to produce a one-side substituted intermediate product (formula V);

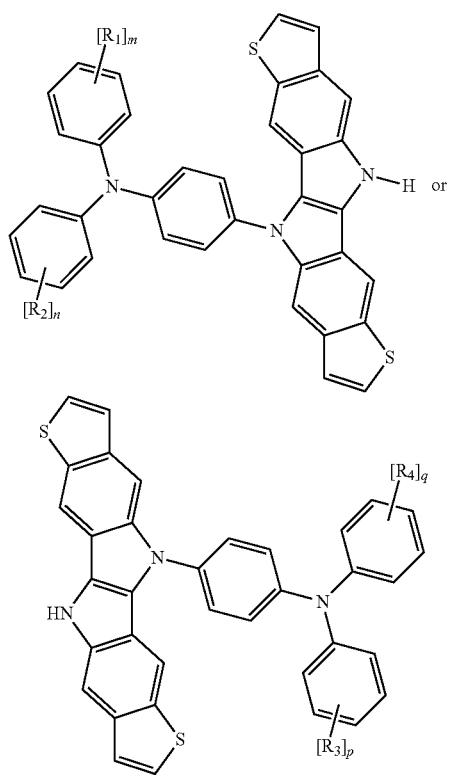

V adding the one-side substituted intermediate product (formula V), triarylamine of the formula IV or III, a catalyst, a base and a solvent into a reaction vessel and mixing them; and
refluxing the obtained mixture under stirring to produce the aromatic amine derivative of the formula I.

9. The preparation method according to claim 8, wherein, the molar ratio of 5,11-disubstituted thieno[3',2':5,6] indolo [3,2-b]thieno [3,2-f] indole (formula II) to the triarylamine of formula III or IV is from 1:1 to 1:2; and the molar ratio of the one-side substituted intermediate product (formula V) to the triarylamine of formula IV or III is from 1:1 to 1:2.

10. The preparation method according to claim 5, wherein, the catalyst comprises a phase transfer catalyst.

11. An organic electroluminescent device comprising a cathode, at least one light emitting unit and an anode, wherein said light emitting unit comprises a hole transporting layer comprising the aromatic amine derivative according to claim 1.

12. The aromatic amine derivative according to claim 2, wherein,
$[R_1]_m$ and $[R_2]_n$ are identical to $[R_3]_p$ and $[R_4]_q$, respectively; and the substitution positions of $[R_1]_m$ and $[R_2]_n$ on the phenyls are identical to those of $[R_3]_p$ and $[R_4]_q$, respectively.

13. The aromatic amine derivative according to claim 2, wherein,
$[R_1]_m$, $[R_2]_n$, $[R_3]_p$ and $[R_4]_q$ are the same, and the substitution positions of $[R_1]_m$, $[R_2]_n$, $[R_3]_p$ and $[R_4]_q$ on the phenyls are the same.

14. The organic electroluminescent device according to claim 11, wherein in the general formula I,
$R_1$, $R_2$, $R_3$ and $R_4$ each independently represent a substituted or unsubstituted $C_1$-$C_6$ alkyl, a substituted or unsubstituted $C_1$-$C_6$ alkoxy, a substituted or unsubstituted $C_3$-$C_6$ cycloalkyl, a substituted or unsubstituted $C_6$-$C_{18}$ aryl group, a substituted or unsubstituted $C_4$-$C_{10}$ heteroaryl containing one or two heteroatoms selected from N, O and S, or a substituted or unsubstituted $C_{10}$-$C_{18}$ fused aryl group formed together with the phenyl group linked therewith;
m, n, p and q each independently represent 0, 1, 2 or 3; and
the substituents are one or more groups selected from the group consisting of a $C_1$-$C_6$ alkyl, a $C_1$-$C_6$ alkoxy or a $C_6$-$C_{18}$ aryl group.

15. The organic electroluminescent device according to claim 11, wherein in the general formula I,
$[R_1]_m$ and $[R_2]_n$ are identical to $[R_3]_p$ and $[R_4]_q$, respectively; and the substitution positions of $[R_1]_m$ and $[R_2]_n$ on the phenyls are identical to those of $[R_3]_p$ and $[R_4]_q$, respectively.

16. The organic electroluminescent device according to claim 11, wherein in the general formula I,
$[R_1]_m$, $[R_2]_n$, $[R_3]_p$ and $[R_4]_q$ are the same, and the substitution positions of $[R_1]_m$, $[R_2]_n$, $[R_3]_p$ and $[R_4]_q$ on the phenyls are the same.

* * * * *